US007094553B2

(12) United States Patent
Prusiner et al.

(10) Patent No.: US 7,094,553 B2
(45) **Date of Patent: *Aug. 22, 2006**

(54) ANTIBODIES SPECIFIC FOR UNGULATE PRP

(75) Inventors: Stanley B. Prusiner, San Francisco, CA (US); Jiri G. Safar, Walnut Creek, CA (US); R. Anthony Williamson, San Diego, CA (US); Dennis R. Burton, La Jolla, CA (US)

(73) Assignees: The Regents of the University of California, Oakland, CA (US); The Scripps Research Institute, La Jolla, CA (US)

( * ) Notice: Subject to any disclaimer, the term of this patent is extended or adjusted under 35 U.S.C. 154(b) by 563 days.

This patent is subject to a terminal disclaimer.

(21) Appl. No.: 10/355,780

(22) Filed: Jan. 30, 2003

(65) Prior Publication Data

US 2003/0143224 A1 Jul. 31, 2003

Related U.S. Application Data

(63) Continuation-in-part of application No. 09/627,218, filed on Jul. 27, 2000, now Pat. No. 6,537,548.

(51) Int. Cl.
*G01N 33/53* (2006.01)

(52) U.S. Cl. .................. 435/7.1; 530/388.1; 530/389.1

(58) Field of Classification Search ................. 435/7.1; 530/388.1, 381.1

See application file for complete search history.

(56) References Cited

U.S. PATENT DOCUMENTS

| | | | |
|---|---|---|---|
| 4,806,627 A | 2/1989 | Wisniewski et al. | |
| 5,792,901 A | 8/1998 | Prusiner et al. | |
| 5,846,533 A | 12/1998 | Prusiner et al. | |
| 5,891,641 A | 4/1999 | Prusiner et al. | |
| 5,908,969 A | 6/1999 | Prusiner et al. | |
| 6,261,790 B1 * | 7/2001 | O'Rourke ................ | 424/130.1 |

FOREIGN PATENT DOCUMENTS

| | | |
|---|---|---|
| GB | EP-0861900 A1 * | 9/1998 |
| WO | WO 99/42829 | 8/1999 |
| WO | WO 99/66956 | 12/1999 |
| WO | WO 01/05426 | 1/2001 |
| WO | WO 01/07479 | 2/2001 |

OTHER PUBLICATIONS

Zanusso et al. Prion protein expression in different species: analysis with a panel of new antibodies. Proceedings of the National Academy of Science USA (1998) vol. 95, pp. 8812-8816.*

Keulen et al. Immunohistochemical detection of prion protein in lymphoid tissue of sheep with natural scrapie. Journal of Clinical Microbiology (1996) vol. 34, No. 5, pp. 1228-1231.*

Harmeyer et al. Synthetic peptide vaccines yield monoclonal antibodies to cellular pathological prion proteins of ruminants. Journal of General Virology (1998) vol. 79, pp. 937-945.*

Meyer et al. Detection of bovine spongiform encephalopathy-specific PrPSc by treatment with heat and guanidine thiocyanate. Journal of Virology (1999) vol. 73, pp. 9386-9392.*

Chapter 3 In: Antibodies: a laboratory manual. Ed. Harlow and Lane. Cold Spring Harbor Laboratory (1988) pp. 23-35.*

Williamson et al. Mapping the prion protein using recombinant antibodies. Journal of Virology (1998) pp. 9413-9418.*

Safar et al., "Eight prion strains have $PrP^{Sc}$ Molecules with different conformations," Nature Medicine, Nature Publishing Co., 4(10):1157-1165 (Oct. 1998).

Peretz et al., "A conformational transition at the N terminus of the prion protein features in formation of the scrapie isoform," Journal of Molecular Biology 273(3):614-622 (Oct. 1997).

Prusiner et al., "Immunologic and Molecular Biologic Studies of Prion Proteins in Bovine Spongiform Encephalopathy" Journal of Infectious Diseases, Chicago, IL, US 167:602-613 (Mar. 1, 1993).

Prusiner et al., "Genetics of Prions" Annual Review of Genetics, Annual Reviews Inc. Palo Alto, CA, US 31:139-175 (1997).

Grathwohl et al. (1997), "Sensitive Enzyme-Linked Immunosorbent Assay for Detection of PrPSc in Crude Tissue Extracts from Scrapie-Affected Mice." *Journal of Virological Methods*, vol. 64:205-216.

Rogers et al. (Apr. 1993), "Conversion of Truncated and Elongated Prion Proteins into the Scrapie Isoform in Cultured Cells." *Proc. Natl. Acad. Sci. USA*, vol. 90:3182-3186.

Scott et al. (Dec. 21, 1999), "Compelling Transgenic Evidence for Transmission of Bovine Spongiform Encephalopathy Prions to Humans." *PNAS*, vol. 96(26): 15137-15142.

Serban et al. (Jan. 1990), "Rapid Detection of Creutzfeldt-Jakob Disease and Scrapie Prion Proteins." *Neurology*, vol. 40:110-116.

Taraboulos et al. (Aug. 1992), "Regional Mapping of Prion Proteins in the Brain." *Proc. Natl. Acad. Sci. USA*, vol. 89:7620-7624.

Tollin et al. (Jun. 1986), "Redox Pathways in Electron/Transfer Proteins: Correlations Between Reactivities, Solvent Exposure, and Unpaired-Spin-Density Distributions." *Proc. Natl. Acad. Sci. USA*, vol. 83:3693-3697.

* cited by examiner

*Primary Examiner*—Ulrike Winkler
(74) *Attorney, Agent, or Firm*—Karl Bozicevic; Bozicevic, Field & Francis LLP

(57) ABSTRACT

The present invention provides antibodies that specifically bind with a high degree of binding affinity to a native ungulate $PrP^{C}$ and/or a denatured ungulate $PrP^{Sc}$, but not to a native ungulate $PrP^{Sc}$. Preferred antibodies find native bovine $PrP^{C}$ and treated $PrP^{Sc}$ but not native bovine $PrP^{Sc}$ and can be used in an assay to determine if a sample is infected with infectious prions, i.e. $PrP^{Sc}$.

24 Claims, 9 Drawing Sheets

FIG. 2A

| | | | | | | | | | | | | | | | |
|---|---|---|---|---|---|---|---|---|---|---|---|---|---|---|---|
| Met | Ala | Asn | Leu | Gly | Tyr | Trp | Leu | Leu | Ala | Leu | Phe | Val | Thr | Met | Trp |
| 1 | | | | 5 | | | | | 10 | | | | | 15 | |
| Thr | Asp | Val | Gly | Leu | Cys | Lys | Lys | Arg | Pro | Lys | Pro | Gly | Gly | Trp | Asn |
| | | | 20 | | | | | 25 | | | | | 30 | | |
| Thr | Gly | Gly | Ser | Arg | Tyr | Pro | Gly | Gln | Gly | Ser | Pro | Gly | Gly | Asn | Arg |
| | | 35 | | | | | 40 | | | | | 45 | | | |
| Tyr | Pro | Pro | Gln | Gly | Gly | Thr | Trp | Gly | Gln | Pro | His | Gly | Gly | Gly | Trp |
| | 50 | | | | | 55 | | | | | 60 | | | | |
| Gly | Gln | Pro | His | Gly | Gly | Ser | Trp | Gly | Gln | Pro | His | Gly | Gly | Ser | Trp |
| 65 | | | | | 70 | | | | | 75 | | | | | 80 |
| Gly | Gln | Pro | His | Gly | Gly | Gly | Trp | Gly | Gln | Gly | Gly | Gly | Thr | His | Asn |
| | | | | 85 | | | | | 90 | | | | | 95 | |
| Gln | Trp | Asn | Lys | Pro | Ser | Lys | Pro | Lys | Thr | Asn | Leu | Lys | His | Val | Ala |
| | | | 100 | | | | | 105 | | | | | 110 | | |
| Gly | Ala | Ala | Ala | Ala | Gly | Ala | Val | Val | Gly | Gly | Leu | Gly | Gly | Tyr | Met |
| | | 115 | | | | | 120 | | | | | 125 | | | |
| Leu | Gly | Ser | Ala | Met | Ser | Arg | Pro | Met | Ile | His | Phe | Gly | Asn | Asp | Trp |
| | 130 | | | | | 135 | | | | | 140 | | | | |
| Glu | Asp | Arg | Tyr | Tyr | Arg | Glu | Asn | Met | Tyr | Arg | Tyr | Pro | Asn | Gln | Val |
| 145 | | | | | 150 | | | | | 155 | | | | | 160 |
| Tyr | Tyr | Arg | Pro | Val | Asp | Gln | Tyr | Ser | Asn | Gln | Asn | Asn | Phe | Val | His |
| | | | | 165 | | | | | 170 | | | | | 175 | |
| Asp | Cys | Val | Asn | Ile | Thr | Ile | Lys | Gln | His | Thr | Val | Thr | Thr | Thr | Thr |
| | | | 180 | | | | | 185 | | | | | 190 | | |
| Lys | Gly | Glu | Asn | Phe | Thr | Glu | Thr | Asp | Val | Lys | Met | Met | Glu | Arg | Val |
| | | 195 | | | | | 200 | | | | | 205 | | | |
| Val | Glu | Gln | Met | Cys | Val | Thr | Gln | Tyr | Gln | Lys | Glu | Ser | Gln | Ala | Tyr |
| | 210 | | | | | 215 | | | | | 220 | | | | |
| Tyr | Asp | Gly | Arg | Arg | Ser | Ser | Ser | Thr | Val | Leu | Phe | Ser | Ser | Pro | Pro |
| 225 | | | | | 230 | | | | | 235 | | | | | 240 |
| Val | Ile | Leu | Leu | Ile | Ser | Phe | Leu | Ile | Phe | Leu | Ile | Val | Gly | (SEQ ID NO: 10) | |
| | | | | 245 | | | | | 250 | | | | | | |

FIG. 2B

Met Val Lys Ser His Ile Gly Ser Trp Ile Leu Val Leu Phe Val Ala
1 5 10 15
Met Trp Ser Asp Val Gly Leu Cys Lys Lys Arg Pro Lys Pro Gly Gly
20 25 30
Trp Asn Thr Gly Gly Ser Arg Tyr Pro Gly Gln Gly Ser Pro Gly Gly
35 40 45
Asn Arg Tyr Pro Pro Gln Gly Gly Gly Gly Trp Gly Gln Pro His Gly
50 55 60
Gly Gly Trp Gly Gln Pro His Gly Gly Gly Trp Gly Gln Pro His Gly
65 70 75 80
Gly Gly Trp Gly Gln Pro His Gly Gly Gly Trp Gly Gln Pro His Gly
85 90 95
Gly Gly Gly Trp Gly Gln Gly Gly Thr His Gly Gln Trp Asn Lys Pro
100 105 110
Ser Lys Pro Lys Thr Asn Met Lys His Val Ala Gly Ala Ala Ala Ala
115 120 125
Gly Ala Val Val Gly Gly Leu Gly Gly Tyr Met Leu Gly Ser Ala Met
130 135 140
Ser Arg Pro Leu Ile His Phe Gly Ser Asp Tyr Glu Asp Arg Tyr Tyr
145 150 155 160
Arg Glu Asn Met His Arg Tyr Pro Asn Gln Val Tyr Tyr Arg Pro Val
165 170 175
Asp Gln Tyr Ser Asn Gln Asn Asn Phe Val His Asp Cys Val Asn Ile
180 185 190
Thr Val Lys Glu His Thr Val Thr Thr Thr Thr Lys Gly Glu Asn Phe
195 200 205
Thr Glu Thr Asp Ile Lys Met Met Glu Arg Val Val Glu Gln Met Cys
210 215 220
Ile Thr Gln Tyr Gln Lys Glu Ser Gln Ala Tyr Tyr Asp Gln Arg Gly
225 230 235 240
Ala Ser Val Ile Leu Phe Ser Ser Pro Pro Val Ile Leu Leu Ile Ser
245 250 255
Phe Leu Ile Phe Leu Ile Val Gly (SEQ ID NO: 11)
260

*y-axis:* ratio $TRF_D/TRF_N$
*x-axis:* dilution of BSE-infected Tg(BoPrP) brain homogenate into 5% normal brain homogenate

*y-axis:* $TRF_D - TRF_N$ (cpm)
*x-axis:* dilution of BSE-infected Tg(BoPrP) brain homogenate into 5% normal brain homogenate

*y-axis:* ratio $TRF_D/TRF_N$
*x-axis:* serial dilution of BSE-infected bovine brain homogenate into 5% normal brain homogenate

*y-axis:* $TRF_D - TRF_N$ (cpm)
*x-axis:* serial dilution of BSE-infected bovine brain homogenate into 5% normal brain homogenate ratio $IHF_D / IHF_N$ dilution of CWD-infected deer brain homogenate
into 5% normal deer brain homogenate $TRF_D - TRF_N$ (cpm)

dilution of CWD-infected deer brain homogenate
into 5% normal deer brain homogenate

ANTIBODIES SPECIFIC FOR UNGULATE PRP

CROSS-REFERENCE

This application is a continuation-in-part application of Ser. No. 09/627,218, filed Jul. 27, 2000, now issued U.S. Pat. No. 6,537,548 on Mar. 25, 2003, which is incorporated herein by reference in its entirety and to which application we claim priority under 35 USC §120.

GOVERNMENT RIGHTS

The United States Government may have certain rights in this application pursuant to Contract No. HL 63817 awarded by the National Institutes of Health.

FIELD OF THE INVENTION

This invention relates to antibodies, methods for obtaining antibodies and assays for using such antibodies. More specifically, the invention relates to ungulate PrP antibodies methods of obtaining antibodies which specifically bind to naturally occurring forms of PrP from ungulates.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not readily infect another (e.g., a mouse).

A major step in the study of prions and the diseases that they cause was the discovery and purification of a protein designated prion protein ("PrP") (Bolton et al. (1982), *Science* 218:1309–11; Prusiner et al. (1982), *Biochemistry* 21:6942–50; McKinley et al.(1983), *Cell* 35:57–62). Complete prion protein-encoding genes have since been cloned, sequenced and expressed in transgenic animals. $PrP^C$ is encoded by a single-copy host gene (Basler et al.(1986), *Cell* 46:417–28) and is normally found at the outer surface of neurons. A leading hypothesis is that prion diseases result from conversion of $PrP^C$ into a modified form called $PrP^{Sc}$.

It appears that $PrP^{Sc}$ is necessary for both the transmission and pathogenesis of the transmissible neurodegenerative diseases of animals and humans. See Prusiner, S. B.(1991), *Science* 252:1515–1522. The most common prion diseases of animals are scrapie of sheep and goats, and bovine spongiform encephalopathy (BSE) of cattle (Wilesmith, J. and Wells (1991), *Microbiol. Immunol.* 172:21–38). Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) (Gajdusek, D. C., (1977) *Science* 197:943–960; Medori et al.(1992), *N. Engl. J. Med.* 326:444–449). The presentation of human prion diseases as sporadic, genetic and infectious illnesses initially posed a conundrum which has been explained by the cellular genetic origin of PrP.

BSE is also a major socioeconomic problem, particularly in Britain. More than 175,000 cattle, primarily dairy cows, have died of BSE during the past decades. Tests conducted by the British government on cattle killed over a 30 month period suggest that about 0.3% of the 749,631 tested, or 2249 cattle may have had BSE even though they did not display any outward symptoms. On Mar. 27, 1996, the European Union (EU) placed a ban on the export of British bovine products, including: live bovine animals, their semen and embryos; meat of bovine animals slaughtered in UK; products obtained from bovine animals slaughtered in UK which are liable to enter the animal feed or human food chain; materials destined for use in medicinal products, cosmetics or pharmaceutical products; and mammalian derived meat and bone-meal. This ban has cost the British farming industry more than 1.5 billion pounds since it was imposed, and left many farmers bankrupt. Although the ban was lifted Aug. 1, 1999, both France and Germany still ban the import of British bovine products, contrary to the EU ruling.

The importance of detecting BSE has been heightened by the possibility that bovine prions have been transmitted to humans who developed new variant Creutzfeldt-Jakob disease (nvCJD) (G. Chazot et al.(1996), *Lancet* 347:1181; R. G. Will et al. (1996), *Lancet* 347:921–925). Earlier studies had shown that the N-terminus of $PrP^{Sc}$ could be truncated without loss of scrapie infectivity (S. B. Prusiner et al. (1982), *Biochemistry* 21:6942–6950; S. B. Prusiner et al. (1984), *Cell* 38:127–134) and correspondingly, the truncation of the N-terminus of $PrP^{Sc}$ still allowed its conversion into $PrP^{Sc}$ (M. Rogers et al.(1993), *Proc. Natl. Acad. Sci. USA* 90:3182–3186). The ability of transmission of nvCJD from cattle to humans has been confirmed through in vivo testing, suggesting that the December 20 issue of Proceedings of National Academy of Sciences undermining the comforting presumption that the documented "species barrier" is relevant to this new strain (M. R. Scott et al. (1999), *Proc. Natl. Acad. Sci. USA* 96:15137–15142).

The presence of $PrP^{Sc}$ in tissues of humans or animals is indicative of prion infection. $PrP^{Sc}$ is the invariant component of prion infection and is the only disease-specific diagnostic marker that can be readily detected by immunoassay in the brains of clinically ill animals and humans Meyer et al. (1986), *Proc. Natl. Acad. Sci. USA*, 83:3693–7; Serban et al. (1990), *Neurology*, 40:110–117; Taraboulos et al. (1992), *Proc. Natl. Acad. Sci. USA*. 89:7620–7624; Grathwohl, K. U. D., M. Horiuchi et al. (1997), *Virol. Methods* 64:205–216. Unfortunately, $PrP^{Sc}$ assays are positive only when the prion titer is high, while detection of low levels of $PrP^{Sc}$ has been problematic. It has also proven difficult to measure low levels of $PrP^{Sc}$ in the presence of high levels of $PrP^C$.

Given the enormity of the potential effect of BSE on the world wide cattle population and the affected cattle population in Great Britain, there is a great need for a method of assessing bovine infection with BSE to protect the cattle populations. Given the potential health risk to the human population, more sensitive methods for detection of bovine prions are urgently needed.

SUMMARY OF THE INVENTION

The present invention provides antibodies that will specifically bind with a high degree of affinity to a native ungulate $PrP^C$ and/or a denatured ungulate $PrP^{Sc}$, but not to a native ungulate $PrP^{Sc}$. The antibodies are also highly specific, i.e. do not bind to other proteins. The antibodies are useful in numerous applications, and particularly for determining prion infection in ungulates. The antibodies are characterized by one or more of the following features (1) an ability to bind to native $PrP^C$ and denatured $PrP^{Sc}$, but not native $PrP^{Sc}$, with specificity, (2) an ability to bind to $PrP^C$ or denatured $PrP^{Sc}$ in situ i.e., will only bind to $PrP^{Sc}$ in a cell culture or in vivo if the prion protein has been treated (e.g.

denatured). Preferred antibodies are further characterized by an ability to (4) bind to a $PrP^C$ protein of only a specific species of mammals e.g., bind to bovine $PrP^C$ and not to $PrP^C$ of other mammals.

An important object is to provide antibodies which bind to a native form of ungulate $PrP^C$.

Another object is to provide antibodies which specifically bind to epitopes of $PrP^C$ of a specific species of animal (e.g. bovine $PrP^C$) and not to the $PrP^C$ of other species of animals (e.g. mouse $PrP^C$).

Still another object is to provide specific methodology to allow others to generate a wide range of specific antibodies characterized by their ability to bind one or more types of $PrP^C$ proteins from one or more species of ungulates.

Another object of the invention is to provide an assay for the detection of $PrP^{Sc}$ in an ungulate using the antibodies of the invention.

An advantage of the invention is that it provides a fast, efficient cost effective assay for detecting the presence of $PrP^{Sc}$ in an ungulate sample.

A specific advantage is that the assay can be used as a screen for the presence of prions (i.e., $PrP^{Sc}$) in products such as pharmaceuticals (derived from natural sources) food, cosmetics or any material which might contain such prions and thereby provide further assurances as to the safety of such products.

Another advantage is that the antibodies can be used with a compound which denatures $PrP^{Sc}$ thereby providing for a means of differentiating levels of $PrP^C$ and $PrP^C$+$PrP^{Sc}$ in a sample.

A feature of the invention is that it uses phage display libraries in the creation of the antibodies.

Another feature of the invention is that the phage are genetically engineered to express a specific binding protein of an antibody on their surface.

An aspect of the invention is to provide a therapeutic antibody which prevents or treats prion disease in ungulates and specifically in cows.

Another aspect of the invention is to provide a means for certifying certain products as being prion free.

These and other aspects, objects, advantages, and features of the invention will become apparent to those persons skilled in the art upon reading the details of the chimeric gene, assay method, and transgenic mouse as more fully described below.

BRIEF DESCRIPTION OF THE DRAWINGS

FIG. 2A shows the amino acid sequence of mouse PrP (SEQ ID NO.: 10) and FIG. 2B shows the amino acid sequence of bovine PrP (SEQ ID NO.: 11).

DETAILED DESCRIPTION OF PREFERRED EMBODIMENTS

Figure 1:
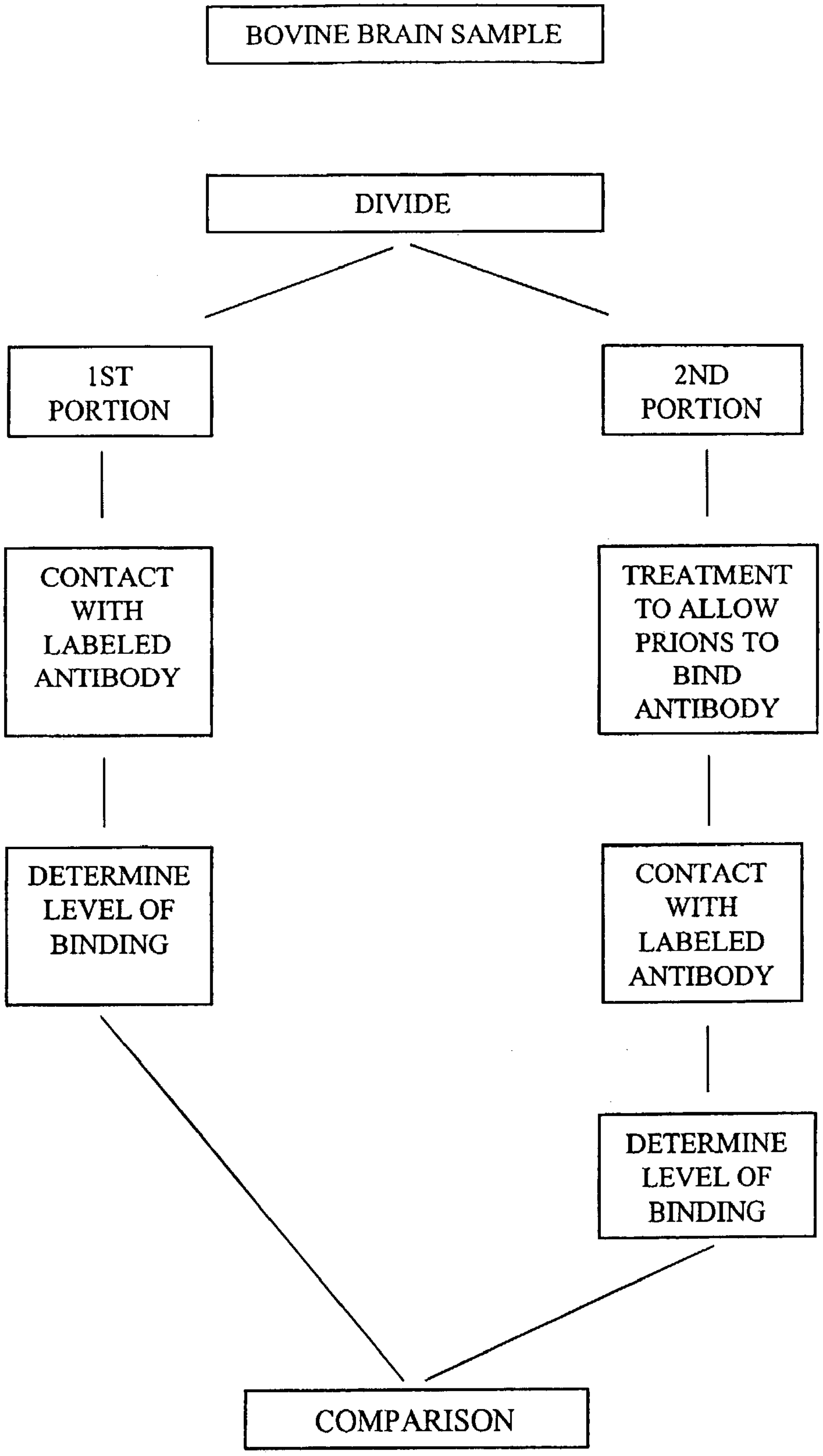
FIG. 1 is a flow diagram of the steps of the conformation-dependant immunoassay (CDI) uses anti-bovine antibodies described and disclosed here.

Before the present antibodies, assays and methods for producing and using such are disclosed and described, it is to be understood that this invention is not limited to particular antibodies, assays or method as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

The terms "PrP protein", "PrP" and the like are used interchangeably herein and shall mean both the infectious particle form $PrP^{Sc}$ known to cause diseases (spongiform encephalopathies) in humans and animals and the non-infectious form $PrP^C$ which, under appropriate conditions is converted to the infectious $PrP^{Sc}$ form.

The terms "prion", "prion protein" and "$PrP^{Sc}$ protein" and the like used interchangeably herein to refer to the infectious $PrP^{Sc}$ form of a PrP protein and is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and chronic wasting disease (CWD) of deer and elk. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The term "PrP gene" is used herein to describe genetic material which expresses $PrP^C$ proteins, including proteins having polymorphisms and mutations such as those listed herein under the subheading "Pathogenic Mutations and Polymorphisms." The term "PrP gene" refers generally to any gene of any species which encodes any form of a prion protein. Some commonly known PrP sequences are described in Gabriel et al. (1992), *Proc. Natl. Acad. Sci. USA* 89:9097–9101, which is incorporated herein by reference to disclose and describe such sequences. The PrP gene can be from any animal including the "host" and "test" animals described herein and any and all polymorphisms and mutations thereof, it being recognized that the terms include other such PrP genes that are yet to be discovered. The protein expressed by such a gene can assume either a $PrP^{C}$ (non-disease) of $PrP^{Sc}$ (disease) form.

The terms "standardized prion preparation", "prion preparation", "preparation" and the like are used interchangeably herein to describe a composition containing prions ($PrP^{Sc}$) which composition is obtained from brain tissue of mammals which contain substantially the same genetic material as relates to prions, e.g., brain tissue from a set of mammals which exhibit signs of prion disease which mammals (1) include a transgene as described herein; (2) have an ablated endogenous prion protein gene; (3) have a high copy number of prion protein gene from a genetically diverse species; or (4) are hybrids with an ablated endogenous prion protein gene and a prion protein gene from a genetically diverse species. The mammals from which standardized prion preparations are obtained exhibit clinical signs of CNS dysfunction as a result of inoculation with prions and/or due to developing the disease due to their genetically modified make up, e.g., high copy number of prion protein genes.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a cow). The genetically altered mammal can be used to assay samples for prions which only infect the genetically diverse mammal. Examples of artificial genes are mouse PrP genes having one or more different replacement codons from cows, sheep and the like replacing mouse codons at the same relative position, with the proviso that not all the mouse codons are replaced with differing human, cow or sheep codons. Artificial PrP genes can include not only codons of genetically diverse animals but may include codons and codon sequences not associated with any native PrP gene but which, when inserted into an animal, render the animal susceptible to infection with prions which would normally only infect a genetically diverse animal.

The terms "chimeric gene", "chimeric PrP gene", "chimeric prion protein gene" and the like are used interchangeably herein to mean an artificially constructed gene containing the codons of a host animal, such as a mouse, with one or more of the codons being replaced with corresponding codons from a genetically diverse test animal, such as a cow or sheep. In one specific example the chimeric gene is comprised of the starting and terminating sequence (i.e., N- and C- terminal codons) of a PrP gene of a mammal of a host species (e.g. a mouse) and also containing a nucleotide sequence of a corresponding portion of a PrP gene of a test mammal of a second species (e.g. a cow). A chimeric gene will, when inserted into the genome of a mammal of the host species, render the mammal susceptible to infection with prions which normally infect only mammals of the second species. The preferred chimeric gene disclosed herein is MBo2M which contains the starting and terminating sequence of a mouse PrP gene and a non-terminal sequence region replaced with a corresponding bovine sequence. The bovine sequence differs from a mouse PrP gene in a manner such that the protein expressed thereby differs at nine residues (see FIG. 2B). MBo2M PrP was constructed as described previously for similar chimeric PrP transgenes (Scott, M., D. Groth et al. (1993), Cell 73: 979–988) and resulting in eight bovine substitutions in MoPrP (position numbers correspond to HuPrP sequence): 97, 109, 138, 143, 145, 155, 184 and 186.

The term "genetic material related to prions" is intended to cover any genetic material which effects the ability of an animal to become infected with prions. Thus, the term encompasses any "PrP gene", "artificial PrP gene", "chimeric PrP gene" or "ablated PrP gene" which terms are defined herein as well as modification of such which effect the ability of an animal to become infected with prions. Standardized prion preparations are produced using animals which all have substantially the same genetic material related to prions so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their PrP gene ablated, i.e., rendered inoperative. The host is inoculated with prion proteins to generate antibodies, and the cells producing the antibodies can be a source of genetic material for making a phage library. Other host animals can have a natural (PrP) gene or one which is altered by the insertion of an artificial gene or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with the ability to infect test animal. For example, the test animal may be any ungulate or mammal infected with a variant ungulate prion, including human, cow, sheep, pig, horse, cat, dog or chicken, and one may wish to determine whether a particular sample includes prions which would normally infect only the test animal.

The terms "genetically diverse animal" and "genetically diverse mammal" are used herein to describe an animal which includes a native PrP codon sequence of the host animal differing from the genetically diverse test animal by 17 or more codons, preferably 20 or more codons, and most preferably 28–40 codons. Thus, a mouse PrP gene is genetically diverse with respect to the PrP gene of a cow or sheep, but is not genetically diverse with respect to the PrP gene of a hamster.

The terms "ablated PrP protein gene", "disrupted PrP gene", and the like are used interchangeably herein to mean an endogenous PrP gene which has been altered (e.g., added and/or removed nucleotides) in a manner so as to render the gene inoperative. Examples of non-functional PrP genes and methods of making such are disclosed in Büieler, H., et al. (1992), *Nature* 356, 577–582 and Weissman (WO 93/10227). The methodology for ablating a gene is taught in Capecchi (1987), *Cell* 51:503–512, all of which are incorporated herein by reference. Preferably both alleles of the genes are disrupted.

The terms "hybrid animal", "transgenic hybrid animal" and the like are used interchangeably herein to mean an animal obtained from the cross-breeding of a first animal having an ablated endogenous prion protein gene with a second animal which includes either (1) a chimeric gene or artificial PrP gene or (2) a PrP gene from a genetically diverse animal. For example a hybrid mouse is obtained by cross-breeding a mouse with an ablated mouse gene with a mouse containing (1) bovine or other ungulate PrP genes (which may be present in high copy numbers) or (2) chimeric mouse/ungulate PrP genes. The term hybrid includes any offspring of a hybrid including inbred offspring of two hybrids provided the resulting offspring is susceptible to infection with prions with normal infect only a genetically diverse species. A hybrid animal can be inoculated with prions and serve as a source of cells for the creation of hybridomas to make monoclonal antibodies of the invention.

The terms "susceptible to infection" and "susceptible to infection by prions" and the like are used interchangeably herein to describe a transgenic or hybrid test animal which develops a disease if inoculated with prions which would normally only infect a genetically diverse test animal. The terms are used to describe a transgenic or hybrid animal such as a transgenic mouse Tg(MBo2M) which, without the chimeric PrP gene, would not become infected with a bovine prion but with the chimeric gene is susceptible to infection with bovine prions.

The term "ungulate" as used herein refers to any hoofed mammal. This includes, but is not limited to, cows, deer, elk, sheep and goats. For purposes of the invention a preferred ungulate is a cow.

By "antibody" is meant an immunoglobulin protein which is capable of binding an antigen. Antibody as used herein is meant to include the entire antibody as well as any antibody fragments (e.g. $F(ab')_2$, Fab', Fab, Fv) capable of binding the epitope, antigen or antigenic fragment of interest.

Antibodies of the invention are immunoreactive or immunospecific for and therefore specifically and selectively bind to an ungulate $PrP_C$ protein. Antibodies which are immunoreactive and immunospecific for natural or native $PrP^C$ are preferred. Antibodies for $PrP^C$ are preferably immunospecific—i.e., not substantially cross-reactive with related materials. Although the term "antibody" encompasses all types of antibodies (e.g., monoclonal) the antibodies of the invention are preferably produced using the phage display methodology described herein.

By "purified antibody" is meant one which is sufficiently free of other proteins, carbohydrates, and lipids with which it is naturally associated. Such an antibody "preferentially binds" to a native $PrP^C$ protein, a denatured $PrP^{Sc}$, or an antigenic fragment of each, i.e., does not substantially recognize and bind to other antigenically-unrelated molecules, including native $PrP^{Sc}$. A purified antibody of the invention is preferably immunoreactive with and immunospecific for a $PrP^C$ protein of specific species and more preferably immunospecific for native bovine PrP.

By "antigenic fragment" of a PrP protein is meant a portion of such a protein which is capable of binding an antibody of the invention.

By "binds specifically" is meant high avidity and/or high affinity binding of an antibody to a specific polypeptide i.e., epitope of a PrP protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to ungulate $PrP^C$ than to other proteins, including $PrP^C$ from mammals such as humans, dogs, cats, etc. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to ungulate $PrP^C$ with a binding affinity of $10^7$ liters/mole or more, preferably $10^8$ liters/mole or more are said to bind specifically to $PrP^C$. In general, an antibody with a binding affinity of $10^6$ liters/mole or less is not useful in that it will not bind an antigen at a detectable level using conventional methodology currently used.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diamin-obenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly an ungulate, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease.

Abbreviations used herein include:

CNS for central nervous system;

BSE for bovine spongiform encephalopathy;

CWD for chronic wasting disease of deer or elk;

CJD for Creutzfeldt-Jakob Disease;

FFI for fatal familial insomnia;

GSS for Gerstmann-Strassler-Scheinker Disease;

Hu for human;

HuPrP for a human prion protein;

Mo for mouse;

MoPrP for a mouse prion protein;

SHa for a Syrian hamster;

SHaPrP for a Syrian hamster prion protein;

Bov for cow;

BovPrP for a cow prion protein;

Tg for transgenic;

Tg(SHaPrP) for a transgenic mouse containing the PrP gene of a Syrian hamster;

Tg(HuPrP) for transgenic mice containing the complete human PrP gene;

Tg(ShePrP) for transgenic mice containing the complete sheep PrP gene;

Tg(BovPrP) for transgenic mice containing the complete cow PrP gene;

$PrP^{Sc}$ for the scrapie isoform of the prion protein;

$PrP^{C}$ for the cellular contained common, normal isoform of the prion protein;

$MoPrP^{Sc}$ for the scrapie isoform of the mouse prion protein;

MHu2M for a chimeric mouse/human PrP gene wherein a region of the mouse PrP gene is replaced by a corresponding human sequence which differs from mouse PrP at 9 codons;

Tg(MHu2M) mice are transgenic mice of the invention which include the chimeric MHu2M gene;

MBo2M for a chimeric mouse/human PrP gene wherein a region of the mouse PrP gene is replaced by a corresponding bovine sequence which differs from mouse PrP at 9 codons;

Tg(MBo2M) mice are transgenic mice of the invention which include the chimeric MBo2M gene;

MBo2M $PrP^{C}$ for the scrapie isoform of the chimeric bovine/mouse PrP gene;

$PrP^{CJD}$ for the CJD isoform of a PrP gene;

$Prnp^{0/0}$ for ablation of both alleles of an endogenous prion protein gene, e.g., the MoPrP gene;

Tg($SHaPrP^{+/0}$)81/$Prnp^{0/0}$ for a particular line (81) of transgenic mice expressing SHaPrP, +/0 indicates heterozygous;

Tg(BovPrP)/$Prnp^{0/0}$ for a hybrid mouse obtained by crossing a mouse with a bovine prion protein gene (BovPrP) with a mouse with both alleles of the endogenous prion protein gene disrupted;

Tg(MBo2M)/$Prnp^{0/0}$ for a hybrid mouse obtained by crossing a mouse with a chimeric prion protein gene (MHu2M) with a mouse with both alleles of the endogenous prion protein gene disrupted.

FVB for a standard inbred strain of mice often used in the production of transgenic mice since eggs of FVB mice are relatively large and tolerate microinjection of exogenous DNA relatively well.

General Aspects of the Invention

The present invention provides an antibody which specifically binds to an ungulate (e.g., cow, sheep or deer) $PrP^{C}$ or denatured ungulate $PrP^{Sc}$, but not to native ungulate $PrP^{Sc}$. More specifically, the methods of the invention provide for the development of antibodies that are able to recognize epitopes that are unavailable on the abnormal conformers of the prion protein, and in particular of the prion protein from ungulates such as cows, sheep and deer. The antibodies and detection methods of the invention allow the quantitative distinguishment between the infectious and noninfectious state of abnormal isoforms of prion protein, as well as between the abnormal and normal isoforms of the prion protein. Preferably, the antibodies bind to a denatured ungulate $PrP^{Sc}$ protein in situ with an affinity of $10^7$ liters/mole or more, preferably $10^8$ liters/mole or more of a single species. Antibodies of the invention may have an affinity for multiple species, e.g., multiple ungulates, or may be specific to a single species, e.g., cow. The antibodies recognize an epitope of the $PrP^{C}$ or denatured $PrP^{Sc}$ that is unavailable in the native form of $PrP^{Sc}$, presumably due to the conformational difference between $PrP^{C}$ and $PrP^{Sc}$. Antibodies may be isolated, using the protocols of the present invention, with the ability to bind to all proteins coded by the different mutations and/or polymorphisms of the ungulate PrP protein gene. Alternatively, a battery of antibodies (2 or more different antibodies) can be provided wherein each antibody of the battery specifically binds to a protein encoded by a different mutation or polymorphism of an ungulate PrP gene. Thus, the antibody can be bound to a support surface and used to assay a sample in vitro for the presence of a particular allele of ungulate $PrP^{C}$.

The antibodies of the present invention are characterized in part by isolation using a phage display library. Construction of phage display libraries for expression of antibodies, particularly the Fab portion of antibodies, is well known in the art. Preferably, the phage display antibody libraries that express antibodies are prepared according to the methods described in U.S. Pat. No. 5,223,409, issued Jun. 29, 1993 and U.S. patent application Ser. No. 07/945,515, filed Sep. 16, 1992, both incorporated herein by reference. Procedures of the general methodology can be adapted using the present disclosure to produce antibodies of the present invention.

The present invention includes a method for panning and screening of antibodies developed against short synthetic peptides that correspond to the hidden epitopes of $BoPrP^{Sc}$ and in particular residues 90–120, which is designated as epitope I.

The antibodies of the present invention are especially useful to detect prions utilizing in vitro methods, in which the presence of $PrP^{Sc}$ in tissues of humans or animals indicates prion infection. A conformation-dependent immunoassay (CDI) offers a rapid, specific, and highly sensitive method for the detection of ungulate $PrP^{Sc}$ using the antibodies of the invention. The assay, as the name indicates, is conformation-sensitive and can detect relatively low levels of $PrP^{Sc}$ in brain homogenates in which $PrP^{C}$ is present in a 100-fold excess. Prior to the present invention, rapid application of CDI for early detection of BSE prions in different tissues of cows was complicated by the lack of high-affinity antibody reacting within the residues 90–120 (epitope I) of the denatured bovine PrP. All the monoclonal or recombinant antibodies generated prior to the invention have either low affinity for bovine PrP or recognize epitopes distant from epitope I. This epitope is critical not only for absolute detection of bovine PrP, but also for conformational sensitivity of CDI. Conformational sensitivity of CDI is crucial for specificity of the assay and the ability to distinguish $PrP^{Sc}$ from $PrP^{C}$. The methods of the invention provide the rational development and specific selection of high-affinity anti-$PrP^{C}$ ungulate antibodies that can be used in, among other things, conformation-dependent immunoassays (CDI), for example, in assays for wild type and de novo bovine, sheep, and deer prions.

A CDI assay is described in U.S. Pat. No. 5,891,641 issued Apr. 6, 1999 and incorporated herein by reference in its entirety. The basic steps of a CDI assay are shown in the flow diagram of FIG. 1. A sample which is preferably a bovine brain sample is divided into two portions. The first portion is contacted with an antibody of the invention which is preferably attached to a detectable label. The level of binding to the bovine $PrP^{C}$ is then determined. The second portion of the sample is then treated in a manner which exposes an epitope which the antibody will bind to, i.e. denaturing proteins within the sample. The treatment exposes epitopes on $PrP^{Sc}$ making it possible for the antibodies to bind the treated $PrP^{Sc}$. Thus, if the sample had $PrP^{Sc}$ in it, the level of binding to the second, treated portion will be higher as compared to the level of binding to the first, untreated portion. The treatment can cause increased levels of binding to $PrP^C$. Thus, some increase is expected even when there is no $PrP^{Sc}$ in the second portion. This makes it necessary to adjust the level of binding on the second, treated portion downward some standard amount. After making the downward adjustment, the level is compared to the level obtained with the first portion and a determination is made as to whether $PrP^{Sc}$ is present in the sample.

Using the present methods, three recombinant antibody fragments (Fabs) were isolated that bind tightly to denatured $BoPrP^{Sc}$ but not to the native conformation of the same protein in CDI-formatted ELISA. All three Fabs were generated against the 96–105 region of bovine prion protein. Clones "O" and "S" recognized only bovine PrP, while clone "P" bound SHa, Mo, Ov, and Hu, as well as bovine $PrP^{Sc}$. The "O" and "P" recombinant antibody fragments (Fabs) were isolated from a mouse cDNA and cloned into a vector that expresses human-mouse (HuM) chimeric Fabs in *E. coli*. The purified Fabs were then labeled with Europium and used in the conformation dependent immunoassay (CDI) to measure bovine, sheep, and deer $PrP^{Sc}$. The transgenic mice expressing bovine $PrP^{Sc}$ will be used in the future for calibration of the CDI sensitivity with respect of the infectious units.

The selection of antibodies and resultant assays can be performed directly in samples or indirectly in the brains of animals innoculated with a sample containing prions.

Although there are known procedures for producing antibodies from any given antigen, practice has shown that it is particularly difficult to produce antibodies which bind to certain proteins e.g., $PrP^C$. The difficulty with obtaining antibodies to $PrP^C$ (and to $PrP^{Sc}$) relates, in part, to its structural qualities. By following procedures described herein antibodies which bind ungulate $PrP^C$ have been obtained and others may follow the procedures described here to obtain other antibodies to $PrP^C$ and to other proteins (e.g. $PrP^C$ proteins from other species) for which it is difficult to generate antibodies.

To produce antibodies of the invention it is preferable to begin with inoculating a host mammal with an innoculum from the desired ungulate $PrP^C$. The host mammal may be any mammal and is preferably a host mammal of the type defined herein such as a mouse, rat, rabbit, guinea pig or hamster, and is most preferably a mouse. The host animal is inoculated with prion proteins which are endogenous to a ungulate species. For example a mouse is inoculated with a bovine $PrP^C$ peptide. Using a normal host mammal in this manner it is possible to elicit the generation of some antibodies. However, since the host animal includes a prion protein gene and is inoculated with $PrP^C$ from a genetically diverse species, the antibodies will, if at all, only be generated for epitopes which differ between epitopes of the prion protein of the host animal and epitopes of the $PrP^C$ from the genetically diverse species. This substantially limits the amount of antibodies which might be generated and decreases the ability to find an antibody which selectively binds to an ungulate $PrP^C$. Thus, in attempting to generate antibodies which differentiate between prion proteins of different species it is preferable to begin the antibody production process using a mammal with an intact endogenous PrP gene.

Antibodies can also be generated in animals which have an ablated prion protein gene, i.e., a null PrP gene abbreviated as $Prnp^{0/0}$. This allows antibodies to be generated against areas of an ungulate $PrP^C$ that are conserved between the host animal and the ungulate PrP genes. Accordingly, the invention is also described in connection with the use of such "null" mammals and more specifically described in connection with "null mice."

A null mouse can be created by inserting a segment of DNA into a normal mouse PrP gene and/or removing a portion of the gene to provide a disrupted PrP gene. The disrupted gene is injected into a mouse embryo and replaces the endogenous PrP gene via homologous recombination.

The null mouse is injected with ungulate PrP peptides to stimulate the formation of antibodies. Injections of adjuvants can be used in conjunction with the peptides to maximize the generation of antibodies. The mouse is then sacrificed and bone marrow and spleen cells are removed. The cells are lysed, RNA is extracted and reversed transcribed to cDNA. Antibody heavy and light chains (or parts thereof) are then amplified by PCR. The amplified cDNA library may be used as is, or further manipulated to create a range of variants and thereby increase the size of the library.

An IgG phage display library is constructed by inserting the amplified cDNA encoding IgG heavy chain and the amplified cDNA encoding a light chain into a phage display vector (e.g., a pComb3 vector) such that one vector contains a cDNA insert encoding a heavy chain fragment in a first expression cassette of the vector, and a cDNA insert encoding a light chain fragment in a second expression cassette of the vector.

Ligated vectors are packaged by a phage display vector such as filamentous phage M13 using methods well known in the art. The packaged library is used to infect a culture of *E. Coli*, to amplify the number of phage particles. After bacterial cell lysis, the phage particles are isolated and used in a panning procedure. The library created is panned against a composition containing the appropriate prions. Antibody fragments which selectively bind to $PrP^{Sc}$ e.g., bovine $PrP^{Sc}$ are then isolated.

Obtaining Antibodies—Generalized Procedure

Antibodies of the invention can be obtained by a variety of techniques. One particular embodiment provides a method for generating antibodies using a library of proteins (i.e., antibodies or portions thereof) on the surface of phage. The library is brought into contact with a composition which includes PrP proteins, and in particular is a naturally occurring composition which includes $PrP^C$. The phage which bind to $PrP^C$ are identified and the antibody or portion thereof which binds the $PrP^C$ protein is isolated. It is desirable to determine the sequence of the genetic material encoding the antibody or portion thereof. Further, the sequence can be amplified and inserted, by itself or with other genetic material, into an appropriate vector and cell line for the production of additional antibodies. For example, a sequence encoding a variable region which binds an epitope of $PrP^C$ hidden in $PrP^{Sc}$ can be fused with a sequence which encodes an ungulate (e.g., bovine) constant region of an antibody to produce a constant/variable construct. This construct can be amplified and inserted into a suitable vector and transfected into a suitable cell line for the production of antibodies. Procedures such as this are described within U.S. Pat. No. 4,816,567, issued Mar. 28, 1989 to Cabilly, et al which is incorporated herein by reference to disclose and describe such procedures. Further, see Bobrzecka et al. (1980) *Immunology Letters*, 2, pages 151–155 and Konieczny et al. (1981) *Haematologia* 14 (1), pages 85–91, also incorporated herein by reference.

When the genetic material encoding an antibody or portion thereof which binds a $PrP^C$ protein is isolated, it is possible to use that genetic material to produce other antibodies or portions thereof which have a greater affinity for binding $PrP^C$ proteins. This is done by site directed mutagenesis technology or by random mutagenesis and selection. Specifically, individual codons or groups of codons within the sequence can be removed or replaced with codons which encode different amino acids. Large numbers of different sequences can be generated, amplified and used to express variations of the antibody or portions thereof on the surface of additional phage. These phage can then be used to test for the binding affinity of the antibody to PrP proteins.

The phage library can be created in a variety of different ways. In accordance with one procedure, a host animal such as a mouse or rat is immunized with $PrP^C$ protein. The immunization may be carried out with an adjuvant to optimize for larger amounts and types of antibodies. After allowing for sufficient time for the generation of antibodies, cells responsible for antibody production are extracted from the inoculated host mammal. RNA is isolated from the extracted cells and subjected to reverse transcription in order to produce a cDNA library. The extracted cDNA is amplified by the use of primers and inserted into an appropriate phage display vector. The vector allows the expression of antibodies or portions thereof on the phage surface. It is also possible to subject the cDNA to site directed mutagenesis prior to insertion into the display vector. Specifically, codons can be removed or replaced with codons expressing different amino acids in order to create a larger library (i.e., a library of many variants) which is then expressed on the surface of the phage. Thereafter, as described above, the phage are brought into contact with the sample and phage which bind to PrP protein are isolated.

Isolation of RNA Encoding Prion-Specific Antibodies

Combinatorial antibody library technology, e.g., antigen based selection from antibody libraries expressed on the surface of M13 filamentous phage, offers a new approach to the generation of monoclonal antibodies and possesses a number of advantages relative to hybridoma methodologies which are particularly pertinent to the present invention (Huse, W. D., L. Sastry et al. (1989) *Science* 246:1275–1281.; Barbas, C. F., III, A. S. Fang, et al. (1991) *Proc. Natl. Acad. Sci. USA* 88:7978–7982.; Burton, D. R. and C. F. Barbas, III (1994) *Adv. Immunol.* 57:191–280).

The present invention provides methods utilizing such technology to provide PrP-specific monoclonal antibodies from phage antibody libraries prepared from BovPrP-immunized $Prnp^{0/0}$ mice. The invention provides the first monoclonal antibodies recognizing BovPrP in situ and demonstrates the application of combinatorial libraries for cloning specific antibodies from null mice. The present invention circumvents problems of tolerance and more efficiently generates panels of monoclonal antibodies capable of recognizing diverse epitopes on Bov PrP and other PrPs in part using null mice. $Prnp^{0/0}$ mice will develop IgG serum titers against Mo, Bov and human PrP following immunization with relatively small quantities of purified respective PrP 27–30 in adjuvant. After allowing sufficient time to generate antibodies, the immunized $Prnp^{0/0}$ mice are sacrificed for hybridoma production in the conventional manner. Fusions derived from these mice secrete $PrP^C$ specific antibody. The general methodologies involved in creating large combinatorial libraries using phage display technology are described and disclosed in U.S. Pat. No. 5,223,409 issued Jun. 29, 1993, which patent is incorporated herein by reference to disclose and describe phage display methodology.

In general, the phage display anti-PrP antibody libraries are prepared by first isolating a pool of RNA that contains RNA encoding anti-PrP antibodies. To accomplish this, an animal (e.g., a mouse, rat, or hamster) is immunized with protein or peptide of interest. However, normal animals do not produce antibodies to prions at detectable or satisfactorily high levels. This problem is avoided by immunizing animals in which the (PrP) gene has been ablated on both alleles. Such mice are designated $Prnp^{0/0}$ and methods for making such mice are disclosed in Bueler et al. (1992) *Nature* 356:577–582 and in Weismann Publication WO 93/10227, published May 27, 1993. Inoculation of null animals with $PrP^C$ or a peptide of $PrP^C$ results in production of IgG serum titers against the prion (Prusiner et al. PNAS 1993). In one preferred embodiment, the animal selected for immunization is a $Prnp^{0/0}$ mouse described by Büeler and Weismann. Generally, the amount of protein necessary to elicit a serum antibody response in a "null" animal is from about 0.01 mg/kg to about 500 mg/kg.

The PrP protein is generally administered to the animal by injection, preferably by intravenous injection, more preferably by intraperitoneal injection. The animals are injected once, with at generally 1 to 4 subsequent booster injections, preferably at least 3 booster injections. After immunization, the reactivity of the animal's antisera with the prion can be tested using standard immunological assays, such as ELISA or Western blot, according to methods well known in the art (see, for example, Harlow and Lane, 1988, *Antibodies: A Laboratory Manual*, Cold Spring Harbor Laboratory Press, Cold Spring Harbor, N.Y.). Animals having prion-binding antisera may be boosted with an additional injection of $PrP^C$.

Serum antibody levels are predictive of antibody secretion, and therefore of levels of specific mRNA in lymphocytes, particularly plasma cells. Detection of serum antibodies, particularly relatively high levels of serum antibodies, is thus correlated to a high level of lymphocytes such as plasma cells producing mRNA encoding those serum antibodies. Thus, plasma cells isolated from the $PrP^C$ immunized mice will contain a high proportion of lymphocytes (e.g., plasma cells) producing prion-specific antibody, particularly when the plasma cells are isolated from the mice within a short time period after the final injection boost (e.g., about 2 to 5 days, preferably 3 days). Immunization of the mice and the subsequent injection boosters thus serve to increase the total percentage of anti-$PrP^C$ antibody-producing plasma cells present in the total population of the mouse's plasma cells. Moreover, because the anti-$PrP^C$ antibodies are being produced at or near peak serum levels, then anti-PrP antibody-producing plasma cells are producing anti-$PrP^C$ antibodies, and thus mRNA encoding these antibodies at or near peak levels.

The above correlation between serum levels of antigen-specific antibodies, the number of lymphocytes producing those antigen-specific antibodies, and the amount of total mRNA encoding the antigen-specific antibodies provides a means for isolating a pool of mRNA that is enriched for the mRNA encoding antigen-specific antibodies of interest. Lymphocytes, including plasma cells are isolated from spleen and/or bone marrow from the prion-immunized animals according to methods well known in the art (see, for example, Huse, W. D., L. Sastry et al. (1989) (see comments) *Science* 246:1275–1281). Preferably the lymphocytes are isolated about 2 to 5 days, preferably about 3 days after the final immunization boost. The total RNA is extracted from these cells. Methods for RNA isolation from mammalian cells are well known in the art (see, for example, Sambrook et al., 1989, *Molecular Cloning: A Laboratory Manual*, 2nd Ed., Cold Spring Harbor Laboratory Press, Cold Spring Harbor, N.Y.).

Production of cDNA Encoding Antibodies from Lymphocyte mRNA cDNA can be produced from the isolated RNA using reverse transcriptase according to methods well known in the art (see, for example, Sambrook et al., supra). cDNA encoding antibody heavy chains or light chains can be amplified using the polymerase chain reaction (PCR). The 3' primers used to amplify heavy chain or light chain-encoding cDNAs are based upon the known nucleotide sequences common to heavy chain or light chain antibodies of a specific antibody subclass. For example, one set of primers based upon the constant region of the IgG1 heavy chain-encoding gene can be used to amplify heavy chains of the IgG1 subclass, while another set of primers based upon the constant portion of the IgG1 light chain-encoding gene is used to amplify the light chains of the IgG1 subclass. The 5' primers are consensus sequences based upon examination of a large number of variable sequences in the data base. In this manner, DNA encoding all antibodies of a specific antibody class or subclass can be amplified regardless of antigen-specificity of the antibodies encoded by the amplified DNA. The entire gene encoding the heavy chain or the light chain can be amplified. Alternatively, only a portion of the heavy or light chain encoding gene may be amplified, with the proviso that the product of PCR amplification encodes a heavy or light chain gene product that can associate with its corresponding heavy or light chain and function in antigen binding, i.e., bind selectively to a prion protein. Preferably, the phage display product is an Fab or Fv antibody fragment.

The antibody encoding cDNA selected for amplification may encode any isotope and preferably encode a subclass of IgG. Exemplary mouse IgG subclasses include IgG1, IgG2a, IgG2b, and IgG3. The selection of the specific antibody subclass-encoding cDNA for amplification will vary according to a variety of factors, including, for example, the animal's serum antibody response to the antigen. Preferably, the antibody subclass-encoding cDNA selected for PCR amplification is that antibody subclass for which the animal produced the highest titer of antibody. For example, if the titers of serum IgG1 are higher than any other subclass of IgG detected in the serum antibody response, then cDNA encoding IgG1 is amplified from the cDNA pool.

Preferably, the heavy and light chains are amplified from the plasma cell cDNA to produce two separate amplified cDNA pools: 1) a cDNA pool containing heavy chain cDNA amplimer products, where the heavy chain is of a specific antibody subclass; and 2) a cDNA pool containing light chain cDNA amplimer products, where the light chain is of a specific antibody subclass.

Antibodies from Transgenic Animals

In addition to obtaining genetic material which encodes antibodies by infecting an animal with an antigen and thereafter extracting cells (and their DNA) responsible for antibody production, it is possible to obtain the genetic material by producing a transgenic animal for producing antibodies. The described technology and transgenic animal technology can be used to produce, e.g., chimeric mouse/bovine or fully bovine antibodies. The technology for producing chimeric or wholly foreign immunoglobins involves obtaining from cells of transgenic animals which have had inserted into their germ line a genetic material encoding all or part of an immunoglobin which binds to the desired antigen. Wholly bovine antibodies can be produced from transgenic mice which have had inserted into their genome genetic material encoding bovine antibodies. Similar technology for producing such antibodies from transgenic animals is described within PCT Publication No. WO 90/04036, published Apr. 19, 1990. Further, see Goodhardt et al. (June 1987) *Proc. Natl. Acad. Sci. U.S.A.* 84:4229–4233, and Bucchine et al. (Mar. 26, 1987) *Nature* 326:409–411, all of which are incorporated herein by reference to disclose and describe methods of producing antibodies from transgenic animals.

The invention is largely described herein with respect to null mice i.e., FVB mice with both alleles of the PrP gene ablated. However, other host animals can be used and preferred host animals are mice and hamsters, with mice being most preferred in that there exists considerable knowledge on the production of transgenic animals. Possible host animals include those belonging to a genus selected from Mus (e.g. mice) Rattus (e.g. rats) Oryctolagus (e.g. rabbits) and Mesocricetus (e.g. hamsters) and Cavia (e.g., guinea pigs). In general mammals with a normal full grown adult body weight of less than 1 kg which are easy to breed and maintain can be used.

Vectors for use with Phage Display Antibody Libraries

The heavy chain-encoding cDNAs and the light chain-encoding cDNAs are then preferably inserted into separate expression cassettes of an appropriate vector. Preferably the vector contains a nucleotide sequence encoding and capable of expressing a fusion polypeptide comprising, in the direction of amino- to carboxy-terminus, 1) a prokaryotic secretion signal domain, 2) an insertion site for DNA encoding a heterologous polypeptide (e.g., either the heavy or light chain-encoding cDNA) and in the expression cassette for the heavy chain cDNA 3) a filamentous phage membrane anchor domain.

The vector includes prokaryotic or mammalian DNA expression control sequences for expressing the fusion polypeptide, preferably prokaryotic control sequences. The DNA expression control sequences can include any expression signal for expressing a structural gene product, and can include 5' and 3' elements operatively linked to the expression cassette for expression of the heterologous polypeptide. The 5' control sequence defines a promoter for initiating transcription, and a ribosome binding site operatively linked at the 5' terminus of the upstream translatable sequence. The vector additionally includes an origin of replication for maintenance and replication in a prokaryotic cell, preferably a gram negative cell such as *E. coli*. The vector can also include genes whose expression confers a selective advantage, such as drug resistance, to a prokaryotic or eukaryotic cell transformed with the vector.

The filamentous phage membrane anchor is preferably a domain of the cpIII or cpVIII coat protein capable of associating with the matrix of a filamentous phage particle, thereby incorporating the fusion polypeptide onto the phage surface. The secretion signal is a leader peptide domain of a protein that targets the protein. to the periplasmic membrane of gram negative bacteria. Such leader sequences for gram negative bacteria (such as *E. coli*) are well known in the art (see, for example, Oliver, In Neidhard, F. C. (ed.) (1987) *Escherichia coli* and *Salmonella typhimurium, American Society for Microbiology*, Washington, D.C., 1:56–69).

Filamentous Phage Membrane Anchors for use in the Phage Display Vector

Preferred membrane anchors for the vector are obtainable from filamentous phage M13, fl, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein, and includes a region of hydrophobic amino acid residues for spanning a lipid bilayer membrane and a region of charged amino acid residues normally found at the cytoplasmic face of the membrane and extending away from the membrane. In the page fl, gene VIII coat protein's membrane spanning region comprises the carboxy-terminal 11 residues from 41 to 52 (Ohkawa et al (1981) *J. Biol. Chem*. 256:9951–9958). An exemplary membrane anchor would consist of residues 26 to 40 to cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

The amino acid residue sequence of another preferred membrane anchor domain is derived from the M13 filamentous phage gene III coat protein (also designate cpIII). Gene III coat protein is present on a mature filamentous phage at one end of the phage particle with typically about 4 to 6 copies of the coat protein. Detailed descriptions of the structure of filamentous phage particles, their coat proteins, and particles assembly are found in the reviews by Rached et al. (1986) *Microbiol. Rev*, 50:401–427 and Model et al. (1988) In: *The Bacteriophages*: Vol. 2, R. Calendar, ed., Plenum Publishing Co., pgs. 375–456.

Preferably, the filamentous phage membrane anchor-encoding DNA is inserted 3' of the cDNA insert in the library vector such that the phage membrane anchor-encoding DNA can be easily excised and the vector relegated without disrupting the rest of the expression cassettes of the vector. Removal of the phage membrane anchor-encoding DNA from the vector, and expression of this vector in an appropriate host cell, results in the production of soluble antibody (Fab) fragments. The soluble Fab fragments retain the antigenicity of the phage-bound Fab, and thus can be used in assays and therapies in the manner that whole (non-fragmented) antibodies are used.

The vector for use with the present invention must be capable of expressing a heterodimeric receptor (such as an antibody or antibody Fab). That is, the vector must be capable of independently containing and expressing two separate cDNA inserts (e.g., the heavy chain cDNA and the light chain cDNA). Each expression cassette can include the elements described above, except that the filamentous phage anchor membrane-encoding DNA is present only in the expression cassette for the heavy chain cDNA. Thus, when the antibody or Fab is expressed on the surface of the phage, only the heavy chain polypeptide is anchored to the phage surface. The light chain is not directly bound to the phage surface, but is indirectly bound to the phage via its association with the free portion of the heavy chain polypeptide (i.e., the portion of the heavy chain that is not bound to the phage surface).

Preferably, the vector contains a sequence of nucleotides that allow for directional ligation, i.e., a polylinker. The polylinker is a region of the DNA expression vector that operatively links the upstream and downstream translatable DNA sequence for replication and transport, and provides a site or means for directional ligation of a DNA sequence into the vector. Typically, a directional polylinker is a sequence of nucleotides that defines two or more restriction endonuclease recognition sequences. Upon restriction enzyme cleavage, the two sites yield cohesive termini to which a translatable DNA sequence can be ligated to the DNA expression vector. Preferably, the two cohesive termini are non-complementary and thereby permit directional insertion of the cDNA into the cassette. Polylinkers can. provide one or multiple directional cloning sites, and may or may not be translated during expression of the inserted cDNA.

In a particular embodiment, the expression vector is capable of manipulating in the form of a filamentous phage particle. Such DNA expression vectors additionally contain a nucleotide sequence that defines a filamentous phage origin of replication such that the vector, upon presentation of the appropriate genetic complement, can replicate as a filamentous phage in single stranded replicative form, and can be packaged into filamentous phage particles. This feature provides the ability of the DNA expression vector to be packaged into phage particles for subsequent isolation of individual phage particles (e.g., by infection of and replication in isolated bacterial colonies).

A filamentous phage origin of replication is a region of the phage genome that defines sites for initiation of replication, termination of replication, and packaging of the replicative form produced by replications (see, for example, Rasched et al. (1986) *Microbiol. Rev*. 50:401–427; Horiuchi (1986) *J. Mol. Biol*. 188:215–223). A preferred filamentous phage origin of replication for use in the present invention is an M13, fl, or fd phage origin of replication (Short et al. (1988) *Nucl. Acids Res*. 16:7583–7600). Preferred DNA expression vectors are the expression vectors pCOMB8, pCKAB8, pCOMB2-8, pCOMB3, pCKAB3, pCOMB2-3, pCOMB2-3' and pCOMB3H.

The pComb3H vector is a modified form of pComb3 in which (i) heavy and light chains are expressed from a single Lac promoter as opposed to individual promoters and (ii) heavy and light chains have two different leader sequences (pg1B and ompA) as opposed to the same leader sequence (pHB). Reference for pComb3H Wang, et al (1995) J. Mol. Biol., Inpress. The principles of pComb3H are basically the same as for pComb3.

Production of the Phage Display Antibody Library

After the heavy chain and light chain cDNAs are cloned into the expression vector, the entire library is packaged using an appropriate filamentous phage. The phage are then used to infect a phage-susceptible bacterial culture (such as a strain of *E. coli*) and the phage allowed to replicate and lyse the cells, and the lysate isolated from the bacterial cell debris. The phage lysate contains the filamentous phage expressing on its surface the cloned heavy and light chains isolated from the immunized animal. In general, the heavy and light chains are present on the phage surface as Fab antibody fragments, with the heavy chain of the Fab being anchored to the phage surface via the filamentous phage membrane anchor portion of the fusion polypeptide. The light chain is associated with the heavy chain so as to form an antigen binding site. Method of producing chimeric antibodies are described within U.S. Pat. No. 4,816,567, issued Mar. 28, 1989 to Cabilly, et al. which is incorporated herein by reference to disclose and describe such procedures. Further, See Bobrzecka et al. (1980) *Immunology Letters*, 2, pages 151–155 and Konieczny, et al (1981) *Haematologia* 14 (1) pages 85–91 also incorporated herein by reference.

Selection of $PrP^{C}$-Antigen Specific Fabs from the Phage Display Antibody Library Phage expressing an antibody or Fab that specifically binds a $PrP^{C}$ epitope that is unavailable in $PrP^{Sc}$ can be isolated using any of a variety of protocols for identification and isolation of monoclonal and/or polyclonal antibodies. Such methods include immunoaffinity purification (e.g., binding of the phage to a columna having bound antigen)

and antibody panning methods (e.g., repeated rounds of phage binding to antigen bound to a solid support for selection of phage of high binding affinity to the antigen). Preferably, the phage is selected by panning using techniques that are well known in the art.

An exemplary panning protocol is performed in two cycles. First round of panning is performed against C-terminus biotinylated synthetic peptides corresponding to the bovine residues 90–145. The peptides are immobilized on a substrate to facilitate isolation of all the antibodies, e.g., attached to ELISA plates previously coated to high density with Streptavidin. Following binding of the peptides and isolation of bound clones, the selected phage are panned against a $PrP^C$ protein (e.g., a native ungulate $PrP^C$ or a chimeric mouse/ungulate $PrP^C$). Selected Fab's are expressed in *E. coli* and purified as described (Williamson, R. A., D. Peretz et al. (1996) *Proc. Natl. Acad. Sci. USA* 93:7279–7282; Peretz, D., R. A. Williamson, et al. (1997) *J. Mol. Biol.* 273:614–622).

After identification and isolation of phage expressing anti-$PrP^C$ antibodies, the phage can be used to infect a bacterial culture, and single phage isolates identified. Each separate phage isolate can be again screened using one or more of the methods described above. In order to further confirm the affinity of the phage for the antigen, and/or to determine the relative affinities of the phage for the antigen, the DNA encoding the antibodies or Fabs can be isolated from the phage, and the nucleotide sequence of the heavy and light chains contained in the vector determined using methods well known in the art (see, for example, Sambrook et al., supra).

Isolation of Soluble Fabs from Phage Selected from the Phage Display Antibody Library Soluble antibodies or Fabs can be produced from a modified display by excising the DNA encoding the filamentous phage anchor membrane that is associated with the expression cassette for the heavy chain of the antibody. Preferably, the DNA encoding the anchor membrane is flanked by convenient restriction sites that allow excision of the anchor membrane sequence without disruption of the remainder of the heavy chain expression cassette or disruption of any other portion of the expression vector. The modified vector without the anchor membrane sequence then allows for production of soluble heavy chain as well as soluble light chain following packaging and infection of bacterial cells with the modified vector.

Alternatively, where the vector contains the appropriate mammalian expression sequences the modified vector can be used to transform a eukaryotic cell (e.g., a mammalian or yeast cell, preferably a mammalian cell (e.g., Chinese hamster ovary (CHO) cells)) for expression of the Fab. Where the modified vector does not provide for eukaryotic expression, preferably the vector allows for excision of both the heavy and light chain expression cassettes as a single DNA fragments for subcloning into an appropriate vector. Numerous vectors for expression of proteins in prokaryotic and/or eukaryotic cells are commercially available and/or well known in the art (see, for example Sambrook et al., supra).

Specifics of a PrP Gene and PrP Proteins

The genetic material which makes up the PrP gene is known for a number of different species of animals (see Gabriel et al. (1992), *Proc. Natl. Acad. Sci. USA* 89:9097–9101). Further, there is considerable homology between the PrP genes in different mammals. Although there is considerable genetic homology with respect to PrP genes, the differences are significant in some instances. More specifically, due to small differences in the protein encoded by the PrP gene of different mammals, a prion which will infect one mammal (e.g. a human) will not normally infect a different mammal (e.g. a mouse). Due to this "species barrier", it is not generally possible to use normal animals, (i.e., animal which have not had their genetic material related to PrP proteins manipulated) such as mice to determine whether a particular sample contains prions which would normally infect a different species of animal such as a human. The present invention provides methods for using modified, transgenic animals having ungulate PrP genes or chimeric ungulate PrP gene to detect prions in samples from ungulates. The antibodies of the present invention provide the means by which these ungulate prions can be detected in assays The major component of purified infectious prions, designated PrP 27–30, is the proteinase K resistant core of a larger native protein $PrP^{Sc}$ which is the disease causing form of the ubiquitous cellular protein $PrP^C$. $PrP^{Sc}$ is found only in scrapie infected cells, whereas $PrP^C$ is present in both infected and uninfected cells implicating $PrP^{Sc}$ as the major, if not the sole, component of infectious prion particles. Since both $PrP^C$ and $PrP^{Sc}$ are encoded by the same single copy gene, great effort has been directed toward unraveling the mechanism by which $PrP^{Sc}$ is derived from $PrP^C$. Central to this goal has been the characterization of physical and chemical differences between these two molecules. Properties distinguishing $PrP^{Sc}$ from $PrP^C$ include low solubility (Meyer et al.(1986), *Proc. Natl. Acad. Sci. USA* 83:3693–7), poor antigenicity (Kascsak et al.(1987), "Mouse Polyclonal and Monoclonal Antibody to Scrapie-Associated Fibril Proteins." *J. Virol.* 61(12):3688–3693; Serban et al.(1990), *Neurology* 40:110–117) protease resistance (Oesch et al. (1985), *Cell* 40:735–746) and polymerization of PrP 27–30 into rod-shaped aggregates which are very similar, on the ultrastructural and histochemical levels, to the PrP amyloid plaques seen in scrapie diseased brains (Prusiner, et al (1983) *Cell*). By using proteinase K it is possible to denature $PrP^C$ but not $PrP^{Sc}$. To date, attempts to identify any post-transitional chemical modifications in $PrP^C$ that lead to its conversion to $PrP^{Sc}$ have proven fruitless (Stahl, et al (1993) *Biochemistry*). Consequently, it has been proposed that $PrP^C$ and $PrP^{Sc}$ are in fact conformational isomers of the same molecule.

Conformational description of PrP using conventional techniques has been hindered by problems of solubility and the difficulty in producing sufficient quantities of pure protein. However, $PrP^C$ and $PrP^{Sc}$ are conformationally distinct. Theoretical calculations based upon the amino acid sequences of PrPs from several species have predicted four putative helical motifs in the molecule. Experimental spectroscopic data would indicate that in $PrP^C$ these regions adopt α-helical arrangements, with virtually no β-sheet (Pan, K. M. et al (1993) *PNAS* 90:10962:6). In dramatic contrast, in the same study it was found that $PrP^{Sc}$ and PrP 27–30 possess significant β-sheet content, which is typical of amyloid proteins. Moreover, studies with extended synthetic peptides, corresponding to PrP amino acid residues 90–145, have demonstrated that these truncated molecules may be converted to either α-helical or β-sheet structures by altering their solution conditions. The transition of $PrP^C$ to $PrP^{Sc}$ requires the adoption of β-sheet structure by regions that were previously α-helical.

It is not entirely clear as to why antibodies of the type described in the above cited publications will bind to $PrP^C$ but not to $PrP^{Sc}$. Without being bound to any particular theory it is suggested that such may take place because epitopes which are exposed when the protein is in the $PrP^C$ conformation are unexposed or partially hidden in the $PrP^{Sc}$ configuration—where the protein is relatively insoluble and more compactly folded together. It is pointed out that stating that an antibody binds to $PrP^C$ but not to $PrP^{Sc}$ is not correct in absolute terms (but correct in commonly accepted terms) because some minimal binding to $PrP^{Sc}$ may occur. For purposes of the invention an indication that no binding occurs means that the equilibrium or affinity constant $K_a$ is $10^6$ l/mole or less. Further, binding will be recognized as existing when the $K_a$ is at $10^7$ l/mole or greater preferably $10^8$ l/mole or greater. The binding affinity of $10^7$ l/mole or more may be due to (1) a single monoclonal antibody (i.e., large numbers of one kind of antibodies) (2) a plurality of different monoclonal antibodies (e.g., large numbers of each of five different monoclonal antibodies) or (3) large numbers of polyclonal antibodies. It is also possible to use combinations or (1)–(3).

Antibody/Antigen Binding Forces

The forces which hold an antigen and antibody together are in essence no different from non-specific interactions which occur between any two unrelated proteins i.e., other macromolecules such as human serum albumin and human transferrin. These intermolecular forces may be classified into four general areas which are (1) electrostatic; (2) hydrogen bonding; (3) hydrophobic; and (4) Van der Waals. Electrostatic forces are due to the attraction between oppositely charged ionic groups on two protein side-chains. The force of attraction (F) is inversely proportional to the square of the distance (d) between the charges. Hydrogen bonding forces are provided by the formation of reversible hydrogen bridges between hydrophilic groups such as —OH, $—NH_2$ and —COOH. These forces are largely dependent upon close positioning of two molecules carrying these groups. Hydrophobic forces operate in the same way that oil droplets in water merge to form a single large drop. Accordingly, non-polar, hydrophobic groups such as the side-chains on valine, leucine and phenylalanine tend to associate in an aqueous environment. Lastly, Van der Waals are forces created between molecules which depend on interaction between the external electron clouds.

Further information regarding each of the different types of forces can be obtained from "Essential Immunology" edited by I. M. Roitti (6th Edition) Blackwell Scientific Publications, 1988. With respect to the present invention useful antibodies exhibit all of these forces. It is by obtaining an accumulation of these forces in larger amounts that it is possible to obtain an antibody which has a high degree of affinity or binding strength to the PrP protein and in particular an antibody which has a high degree of binding strength to ungulate $PrP^C$.

Measuring Antibody/Antigen Binding Strength

The binding affinity between an antibody and an antigen can be measured which measurement is an accumulation of a measurement of all of the forces described above. Standard procedures for carrying out such measurements exist and can be directly applied to measure the affinity of antibodies of the invention for PrP proteins including ungulate $PrP^C$.

One standard method for measuring antibody/antigen binding affinity is through the use of a dialysis sac which is a container comprised of a material which is permeable to the antigen but impermeable to the antibody. Antigens which are bound completely or partially to antibodies are placed within the dialysis sac in a solvent such as in water. The sac is then placed within a larger container, which does not contain antibodies or antigen but contains only the solvent e.g., the water. Since only the antigen can diffuse through the dialysis membrane the concentration of the antigen within the dialysis sac and the concentration of the antigen within the outer larger container will attempt to reach an equilibrium. After placing the dialysis sac into the larger container and allowing for time to pass towards reaching an equilibrium it is possible to measure the concentration of the antigen within the dialysis sac and within the surrounding container and then determine the differences in concentration. This makes it possible to calculate the amount of antigen which remains bound to antibody in the dialysis sac and the amount which disassociates from the antibody and diffuses into the surrounding container. By constantly renewing the solvent (e.g., the water) within the surrounding container so as to remove any antigen which is diffused thereinto, it is possible to totally disassociate the antibody from antigen within the dialysis sac. If the surrounding solvent is not renewed the system will reach an equilibrium and it is possible to calculate the equilibrium constant (K) of the reaction i.e., the association and disassociation between the antibody and antigen. The equilibrium constant (K) is calculated as an amount equal to the concentration of antibody bound to antigen within the dialysis sac divided by the concentration of free antibody combining sites times the concentration of free antigen. The equilibrium constant or "K" value is generally measured in terms of liters per mole. The K value is a measure of the difference in free energy (delta g) between the antigen and antibody in the free state as compared with the complexed form of the antigen and antibody. When using the phage display methodology described below, the antibodies obtained have an affinity or K value of $10^7$ liters/mole or more.

Antibody Avidity

As indicated above the term "affinity" describes the binding of an antibody to a single antigen determinate. However, in most practical circumstances one is concerned with the interaction of an antibody with a multivalent antigen. The term "avidity" is used to express this binding. Factors which contribute to avidity are complex and include the heterogeneity of the antibodies in a given serum which are directed against each determinate on the antigen and the heterogeneity of the determinants themselves. The multivalence of most antigens leads to an interesting "bonus" effect in which the binding of two antigen molecules by an antibody is always greater, usually many fold greater, than the arithmetic sum of the individual antibody links. Thus, it can be understood that the measured avidity between an antiserum and a multivalent antigen will be somewhat greater than the affinity between an antibody and a single antigen determinate.

The Conformation-Dependent Assay (CDI)

The Conformation-Dependent Assay; or "CDI" allows the direct measurement of the amount of $PrP^{Sc}$ in brain homogenates without prior digestion with proteinase K to eliminate $PrP^C$. The assay is conformation-sensitive and can detect relatively low levels of $PrP^{Sc}$ in brain homogenates in which $PrP^C$ is present in a 100-fold excess. By selective precipitation of $PrP^{Sc}$ prior to differential immunoassay, $PrP^{Sc}$ can be measured in the presence of a 3,000-fold excess of $PrP^C$. Currently, the assay can quantify less than 1 ng/ml of $PrP^{Sc}$ in brain homogenate with a dynamic range of 5 orders of magnitude (Safar, J., H. Wille et al. (1998), *Nat. Med*, 4(10):1157–1165). Since the prion titer in brain homogenates of clinically ill CJD patients is equal to or lower than $10^6$ $ID_{50}$ units/ml of 5% brain homogenate (unpublished data), the differential immunoassay can detect prion titers as low as 1 $ID_{50}$ unit/ml.

The CDI allows one to distinguish multiple strains of prions by plotting the ratio of denatured/native PrP as a function of $PrP^{Sc}$ concentration before and after limited proteinase K digestion. In contrast, only one strain (DY) (Bessen, R. A. and R. F. Marsh (1994), *J. Virol.* 68:7859–7868) can be distinguished from the other seven strains by Western blotting after limited proteolysis. Moreover, their relativity increased protease sensitivity of $PrP^{Sc}$ in DY prions can lead to an underestimation of its level by immunoblotting (Scott, M. R., D. Groth, et al. (1997), *J. Virol.* 71:9032–9044).

Specifically, the antibodies to ungulate residues 90–120 (epitope I) allow the CDI to detect prions in cows, deer, elk, sheep and other ungulates. The high-affinity antibody reacting within epitope I of the denatured bovine PrP allow the CDI assay to detect, for example, the presence of bovine prions in a test sample. This epitope is critical not only for absolute, but also for conformational sensitivity of CDI. Conformational sensitivity of CDI is crucial for specificity of the assay and the ability to distinguish $PrP^{Sc}$ from $PrP^{C}$.

Pathogenic Mutations and Polymorphisms

There are a number of known pathogenic mutations in the human PrP gene. Further, there are known polymorphisms in the human, sheep and bovine PrP genes. The antibodies of the present invention may be geared to recognize specific alleles of the PrP gene. Alternatively polymorphisms or mutations known to be pathogenic in one species (e.g. human) can be added to a peptide from an ungulate PrP. The following is a list of such mutations and polymorphisms:

| Pathogenic bovine mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

The DNA sequence of the sheep and cow PrP genes have been determined allowing, in each case, the prediction of the complete amino acid sequence of their respective PrP proteins. The normal amino acid sequence which occurs in the vast majority of individuals is referred to as the wild-type PrP sequence. This wild-type sequence is subject to certain characteristic polymorphic variations. In the case of sheep PrP the gene displays two amino acid polymorphisms at residues 171 and 136, while bovine PrP has either five or six repeats of an eight amino acid motif sequence in the amino terminal region of the mature prion protein. While none of these polymorphisms are of themselves pathogenic, they appear to influence prion diseases. Distinct from these normal variations of the wild-type PrP proteins, certain mutations of the human PrP gene which alter either specific amino acid residues of PrP or the number of octarepeats have been identified which segregate with inherited human prion diseases.

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al. (1992) *Proc. Natl. Acad. Sci. USA* 89:9097–9101. The sequence for the Syrian hamster is published in Basler et al. (1986) *Cell* 46:417–428. The PrP gene of sheep is published by Goldmann et al. (1990) *Proc. Natl. Acad. Sci. USA* 87:2476–2480. The PrP gene sequence for bovine is published in Goldmann et al. (1991) *J. Gen. Virol.* 72:201–204. The sequence for chicken PrP gene is published in Harris et al. (1991) *Proc. Natl. Acad. Sci. USA* 88:7664–7668. The PrP gene sequence for mink is published in Kretzschmar et al. (1992) *J. Gen. Virol.* 73:2757–2761. The human PrP gene sequence is published in Kretzschmar et al. (1986) *DNA* 5:315–324. The PrP gene sequence for mouse is published in Locht et al. (1986) *Proc. Natl. Acad. Sci. USA* 83:6372–6376. The PrP gene sequence for sheep is published in Westaway et al. (1994) *Genes Dev.* 8:959–969. These publications are all incorporated herein by reference to disclose and describe the PrP gene and PrP amino acid sequences.

Standardized Prion Preparation

Standardized prion preparations may be produced in order to test assays of the invention and thereby improve the reliability of the assay. Although the preparation can be obtained from any animal it is preferably obtained from a host animal which has brain material containing prions of a test animal. For example, a transgenic mouse containing a bovine prion protein gene can produce bovine prions and the brain of such a mouse can be used to create a standardized bovine prion preparation. Further, in that the preparation is to be a "standard" it is preferably obtained from a battery (e.g., 100; 1,000, or more animals) of substantial identical animals. For example, 100 mice all containing a very high copy number of bovine PrP genes (all polymorphisms and mutations) would spontaneously develop disease and the brain tissue from each could be combined to make a useful standardized prion preparation. Standardized prion preparations are described and disclosed in U.S. Pat. No. 5,908,969 issued Jun. 1, 1999 and U.S. Pat. No. 6,020,537 issued Feb. 1, 2000, both of which are incorporated herein in their entirety.

Standardized prion preparations can be produced using any of modified host mammals of the type described above. For example, standardized prion preparations can be produced using mice, rats, rabbits, hamsters, or guinea pigs which are genetically modified so that they are susceptible to infection with prions which prions would generally only infect genetically diverse species such as a cow, sheep, deer or horse and which modified host mammals will develop clinical signs of CNS dysfunction within a period of time of 350 days or less after inoculation with prions. The most preferred host mammal is a mouse in part because they are inexpensive to use and because a greater amount of experience has been obtained with respect to production of transgenic mice than with respect to the production of other types of host animals. Details regarding making standardized prion preparation are described in U.S. Pat. Nos. 6,008,435 and 6,020,537, both of which are incorporated herein by reference.

Once an appropriate type of host is chosen, such as a mouse, the next step is to choose the appropriate type of genetic manipulation to be utilized to produce a standardized prion formulation. For example, the mice may be mice which are genetically modified by the insertion of a chimeric gene of the invention. Within this group the mice might be modified by including high copy numbers of the chimeric gene and/or by the inclusion of multiple promoters in order to increase the level of expression of the chimeric gene. Alternatively, hybrid mice of the invention could be used wherein mice which have the endogenous PrP gene ablated are crossed with mice which have a bovine PrP gene inserted into their genome. There are, of course, various subcategories of such hybrid mice. For example, the bovine PrP gene may be inserted in a high copy number an/or used with multiple promoters to enhance expression. In yet another alternative the mice could be produced by inserting multiple different PrP genes into the genome so as to create mice which are susceptible to infection with a variety of different prions, i.e., which generally infect two or more types of test animals. For example, a mouse could be created which included a chimeric gene including part of the sequence of a cow, a separate chimeric gene which included part of the sequence of a deer, and still another chimeric gene which included part of the sequence of a sheep. If all three different types of chimeric genes were inserted into the genome of the mouse the mouse would be susceptible to infection with prions which generally only infect a cow, deer and sheep.

After choosing the appropriate mammal (e.g., a mouse) and the appropriate mode of genetic modification (e.g., inserting a chimeric PrP gene such as MBo2M) the next step is to produce a large number of such mammals which are substantially identical in terms of genetic material related to prions. More specifically, each of the mice produced will include an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time e.g., within ±30 days of each other.

Once a large group e.g., 50 or more, more preferably 100 or more, still more preferably 500 or more of such mice are produced. The next step is to inoculate the mice with prions which generally only infect a genetically diverse mammal e.g., prions from an ungulate such as a sheep, cow, deer or horse. The amounts given to different groups of mammals could be varied. After inoculating the mammals with the prions the mammals are observed until the mammals exhibit symptoms of prion infection e.g., clinical signs of CNS dysfunction. After exhibiting the symptoms of prion infection the brain or at least a portion of the brain tissue of each of the mammals is extracted. The extracted brain tissue is homogenized which provides the standardized prion preparation.

As an alternative to inoculating the group of transgenic mice with prions from a genetically diverse animal it is possible to produce mice which spontaneously develop prion related diseases. This can be done, for example, by including extremely high copy numbers of a cow PrP gene into a mouse genome. When the copy number is raised to, for example, 100 or more copies, the mouse will spontaneously develop clinical signs of CNS dysfunction and have, within its brain tissue, prions which are capable of infecting humans. The brains of these animals or portions of the brain tissue of these animals can be extracted and homogenized to produce a standardized prion preparation.

The standardized prion preparations can be used directly or can be diluted and titered in a manner so as to provide for a variety of different positive controls. More specifically, various known amounts of such standardized preparation can be used to inoculate a first set of transgenic control mice. A second set of substantially identical mice are inoculated with a material to be tested i.e., a material which may contain prions. A third group of substantially identical mice are not injected with any material. The three groups are then observed. The third group, should, of course not become ill in that the mice are not injected with any material. If such mice do become ill the assay is not accurate probably due to the result of producing mice which spontaneously develop disease. If the first group, injected with a standardized preparation, do not become ill the assay is also inaccurate because the mice have not been correctly created so as to become ill when inoculated with prions which generally only infect a genetically diverse mammal. However, if the first group does become ill and the third group does not become ill the assay can be presumed to be accurate. Thus, if the second group does not become ill the test material does not contain prions and if the second group does become ill the test material does contain prions.

By using standardized prion preparations of the invention it is possible to create extremely dilute compositions containing the prions. For example, a composition containing one part per million or less or even one part per billion or less can be created. Such a composition can be used to test the sensitivity of the antibodies, assays and methods of the invention in detecting the presence of prions.

Prion preparations are desirable in that they will include a constant amount of prions and are extracted from an isogeneic background. Accordingly, contaminates in the preparations will be constant and controllable. Standardized prion preparations will be useful in the carrying out of bioassays in order to determine the presence, if any, of prions in various pharmaceuticals, products produced by using ungulates including foods, cosmetics, etc.

Useful Applications

As indicated above and described further below in detailed examples it is possible to use the methodology of the invention to create a wide range of different antibodies. i.e., antibodies having different specific features. For example, antibodies can be created which bind only to a $PrP^C$ protein naturally occurring within a single ungulate species and not bind to a $PrP^C$ protein naturally occurring within other species. Further, the antibody can be designed so as to bind only to a non-infectious form of an ungulate prion protein (e.g., $PrP^C$) and not bind to an infectious form (e.g., $PrP^{Sc}$). A single antibody or a battery of different antibodies can then be used to create an assay device. Such an assay device can be prepared using conventional technology known to those skilled in the art. The antibody can be purified and isolated using known techniques and bound to a support surface using known procedures. The resulting surface having antibody bound thereon can be used to assay a sample in vitro to determine if the sample contains one or more types of antibodies.

The antibodies are most useful in carrying out CDI assays of the type described in U.S. Pat. No. 5,891,641. In addition, the antibodies could be used in treatments by binding to $PrP^C$ and thereby preventing it from converting to $PrP^{Sc}$.

Commercial Assays

One embodiment of the invention features commercial assays allowing detection of $PrP^{Sc}$ in an ungulate sample by 1) digesting the sample with an enzyme that effectively degrades $PrP^{C}$ and which denatures $PrP^{Sc}$, or alternatively by successive treatment with an enzyme that degrades $PrP^{C}$ (but not PrPSc) and then an enzyme which denatures $PrP^{Sc}$ and 2) detecting the denatured $PrP^{Sc}$ using an antibody of the present invention. For example, a sample containing bovine PrP proteins (i.e., $PrP^{C}$ and $PrP^{Sc}$) can be subjected to denaturation by the use of proteinase K (PK) digestion. The use of such will digest $PrP^{C}$ but not $PrP^{Sc}$. Following digestion with proteinase K, the sample is further digested to denature the $PrP^{Sc}$, and the sample is contacted with an antibody of the present invention under suitable binding conditions. Preferably, the antibody is bound to a substrate and can be positioned such that the sample can be easily contacted with the substrate material having the antibody bound thereon. If material binds to the antibodies on the substrate the presence of infectious $PrP^{Sc}$ is confirmed.

In another embodiment, a sample to be tested is divided into two portions, and one is digested to denature any $PrP^{Sc}$ in the sample without destroying the $PrP^{C}$ in the sample. Both portions are contacted with an antibody of the invention, which will bind to $PrP^{C}$ in the untreated portion and both $PrP^{C}$ and $PrP^{Sc}$ in the treated portion. Levels of $PrP^{C}$ or $PrP^{C}$+$PrP^{Sc}$ are detected and the amount of $PrP^{Sc}$ in the sample determine from the difference in detectable signal between the two samples.

In commercial embodiments of the invention it may be desirable to use antibodies of the invention in a sandwich type assay. More particularly, the antibody of the invention may be bound to a substrate support surface. The denatured sample to be tested is contacted with the support surface under conditions which allow for binding. Thereafter, unreacted sites are blocked and the surface is contacted with a generalized antibody which will bind to any protein thereon. The generalized antibody is linked to a detectable label. The generalized antibody with detectable label is allowed to bind to any denatured $PrP^{Sc}$ bound to the antibodies on the support surface. If binding occurs the label can be made to become detectable such as by generating a color thereby indicating the presence of the label which indirectly indicates the presence of $PrP^{Sc}$ within the sample. The assay can detect denatured $PrP^{Sc}$ present in an amount of 1 part per million or less, even one part per billion or less. The $PrP^{Sc}$ may be present in a source selected from the group consisting of (a) a pharmaceutical formulation containing a therapeutically active component extracted from an animal source, (b) food products, (c) an organ, tissue, body fluid or cells extracted from a human source, (d) an animal-based product such as injectables, orals, creams, suppositories, and intrapulmonary delivery formulations, (e) a cosmetic, and (f) a pharmaceutically active compound extracted from a mammalian cell culture.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade, and pressure is at or near ambient.

Example 1

Identification and Isolation of Anti-Bovine Antibodies

Antibodies that recognize bovine $PrP^{C}$ or denatured $PrP^{Sc}$ were produced using $Prnp^{0/0}$ mice. Mice were immunized with synthetic bovine $PrP^{C}$ peptide coupled to KLH and corresponding to residues 96–115 of bovine PrP. Phage display libraries were constructed from spleens from mice showing high titers of sera against the homologous antigen. Thereafter, we panned the library against synthetic peptides of varying length and selected over 32 different positive clones. The selected clones were screened by CDI-formatted ELISA and specifically evaluated by Western blot. The mouse was injected with bovine peptides to stimulate the formation of antibodies. The mouse is then sacrificed and bone marrow and spleen cells are removed. The cells are lysed, RNA is extracted and reversed transcribed to cDNA. Antibody heavy and light chains (or parts thereof) and then amplified by PCR. Identified light chain sequences were isolated as follows:

```
Clone P
ELVMTQTPSSLSASLGERVSLTCRASQDIGNNLNWIQQKPDGTIKRLIYATSSLDSGVPKRFSGSRSGSDYSLTISSL  (SEQ ID NO:1)
ESEDFADYYCLQHDTFPLTFGGGTKLEIKRTVAA
```

Heavy chains isolated were as follows:

| | | | | |
|---|---|---|---|---|
| | | | FR2 | |
| Clone P | EVQLLEQSGAELVKPGASVKLSCTASGFNIEDSYIH | | **WVKQRPEQ** | (SEQ ID NO:2) |
| Clone S | EVQLLEQSGAELVRPGASVKLSCTASGFNIEDYYIH | | **WVIQRPGQ** | (SEQ ID NO:3) |
| | FR2 | | FR3 | |
| Clone P | **GLEWIG** | RIDPEDGETKYAPKFQG | **KATITADTSSNTAYLHLRRLTS** | (SEQ ID NO:4) |
| Clone S | **GLEWIG** | RIDPEDGETKYAPKFQD | **KATLTADTSSNTAYLHLRSLTS** | (SEQ ID NO:5) |
| | FR3 | | FR4 | |
| Clone P | **EDTAIYYCGR** | GAYYIKEDF- | **WGQGTTLTVSS**ASTK | (SEQ ID NO:6) |
| Clone S | **EDTAIYFCGR** | NDGLYAGQDY | **WGQGTTLTVSS**ASTK | (SEQ ID NO:7) |

An IgG phage display library was constructed by inserting an amplified cDNA encoding an IgG heavy chain and the amplified cDNA encoding a light chain into a phage display vector (e.g., a pComb3 vector) such that one vector contained a cDNA insert encoding a heavy chain fragment in a first expression cassette of the vector, and a cDNA insert encoding a light chain fragment in a second expression cassette of the vector. Ligated vectors were packaged by filamentous phage M13 using methods well known in the art, and used to infect a culture of *E. coli*, so as to amplify the number of phage particles. After bacterial cell lysis, the phage particles were isolated and used in a panning procedure. The library created was panned against a composition containing bovine prions. Antibody fragments which selectively bind to the bovine $PrP^C$ were then isolated. (Barbas, C. F., III and D. R. Burton (1996) *Trends Biotechnol.* 14: 230–234; Williamson, R. A., D. Peretz, et al. (1996) *Proc. Natl. Acad. Sci. USA* 93:7279–7282.; Williamson, R. A., D. Peretz et al. (1998) *J. Virol.* 72:9413–9418). The epitopes of recombinant mouse Fab's O, P, and S were mapped using a library of synthetic decapeptides corresponding to the BoPrP (90–145) sequence and overlapping by 3 residues. All three Fab's reacted exclusively with single linear epitope within residues 96–105 of bovine PrP. However, the P antibody display broader specificity against similar sequences in other species and the common epitope motive can be summarized as: HG(S,N)QWNKPSKPKTN (SEQ ID NOS: 8 and 9). This epitope is present in all ungulate PrP sequences, including bovine, mule deer, white tail deer, rod deer, elk, camel, kudu, goat, sheep, and pig. Moreover, this epitope is also present in the sequences of PrP from other species such as ferret, cat, mink, chimp, gorilla, orangutan, presbitis, rabbit, mouse, rat, hamster, macaque, spider monkey, squirrel monkey, baboon, and marmoset. Therefore, the P clone is expected to recognize equally well all the above listed PrP's. An antibody using clone P was isolated as Eu-(HuM)Fab P, and an antibody using clone S was isolated as Eu-(HuM)Fab S.

Example 2

Detection of Chimeric Bovine PrP in Mouse Brain Homogenates

The isolated antibodies Eu-(HuM)Fab P and Eu-(HuM) Fab S were tested for sensitivity using the conformation-dependent immunoassay (CDI) to detect chimeric MBo2M PrP. The chimeric recombinant protein rPrP(MBo2M) was diluted into 5% $PrP^{0/0}$ mouse brain homogenate and the two bovine anti-$PrP^C$ antibodies tested for their ability to detect the protein in its native $PrP^C$ form. Briefly, the brains of $Prnp^{0/0}$ mice which do not express PrP protein were homogenized on ice by 3×30 sec strokes of PowerGen homogenizer (Fisher Scientific, Pittsburgh, Pa.) in PBS (pH 7.4). Resulting 10% (w/v) homogenates were spun for 5 min at 500 g at table top centrifuge. The supernatant was mixed 1:1 with 4% Sarcosyl in PBS (pH 7.4). The purified recombinant PrP (MBo2M) was diluted into the homogenate and each sample was divided in two aliquots: (1) untreated and designated native; (2) mixed with final 4M Gdn HCI and heated for 5 min at 80–100° C. and designated denatured. Both samples wore diluted 20-fold by $H_2O$ and aliquots loaded on polystyrene plate activated for 1 hr with 0.2% glutaraldehyde in PBS. The plates, incubated overnight at 5° C., were blocked with TBS (pH 7.8) containing 0.5% BSA (w/v) and 6% Sorbitol (w/v).

Figure 3:
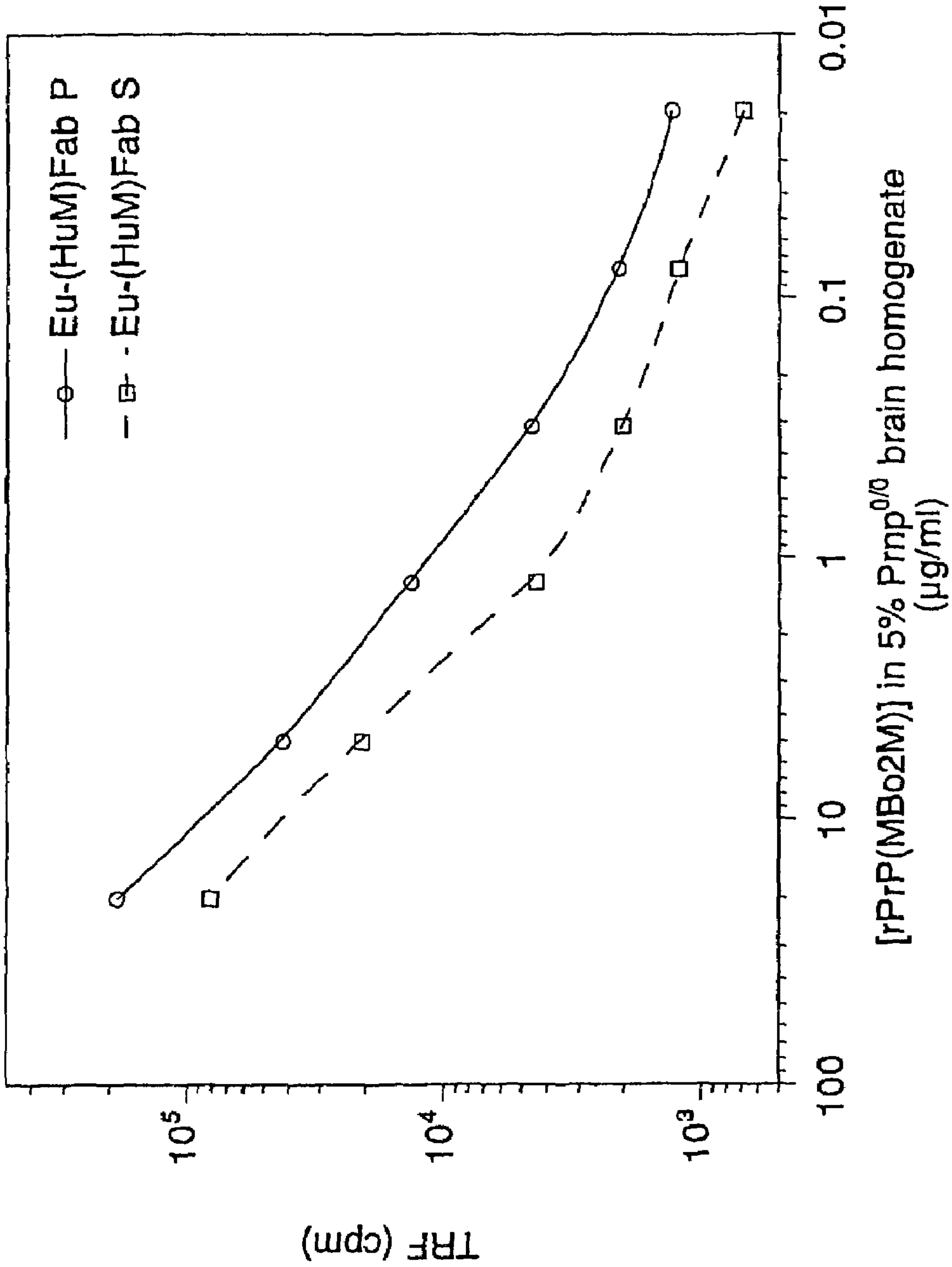
FIG. 3 illustrates the sensitivity of conformation-dependent immunoassay (CDI) in the detection of chimeric MBo2M PrP by Eu-(HuM)Fab P and Eu-(HuM)Fab S.

The samples were washed three time with TBS (pH 7.8) containing 0.05% (v/v) of Tween 20 and incubated for 2 hrs with Europium-labeled chimeric recombinant Fab P and S. The plates were developed after additional washing in enhancement solution provided by the Europium label supplier (Wallac Inc., Turku, Finland) and signal was evaluated with Discovery (Packard Inc.) time-resolved fluorescence spectroscopy. The PrP concentration was calculated as described (Safar, J., H. Willie, et al. (1998) *Nat. Med*, 4(10):1157–1165) and plotted for various antibody concentrations (FIG. 3). The data points and bars represent average concentration±SEM obtained from three independent experiments at an antibody concentration 1 μg/ml. The Europium density in both recombinant antibodies is 4.3 Eu/Fab.

Example 3

Sensitivity of Detection of Bovine $PrP^{sc}$ in Mouse Brain Homogenates

Figure 4:
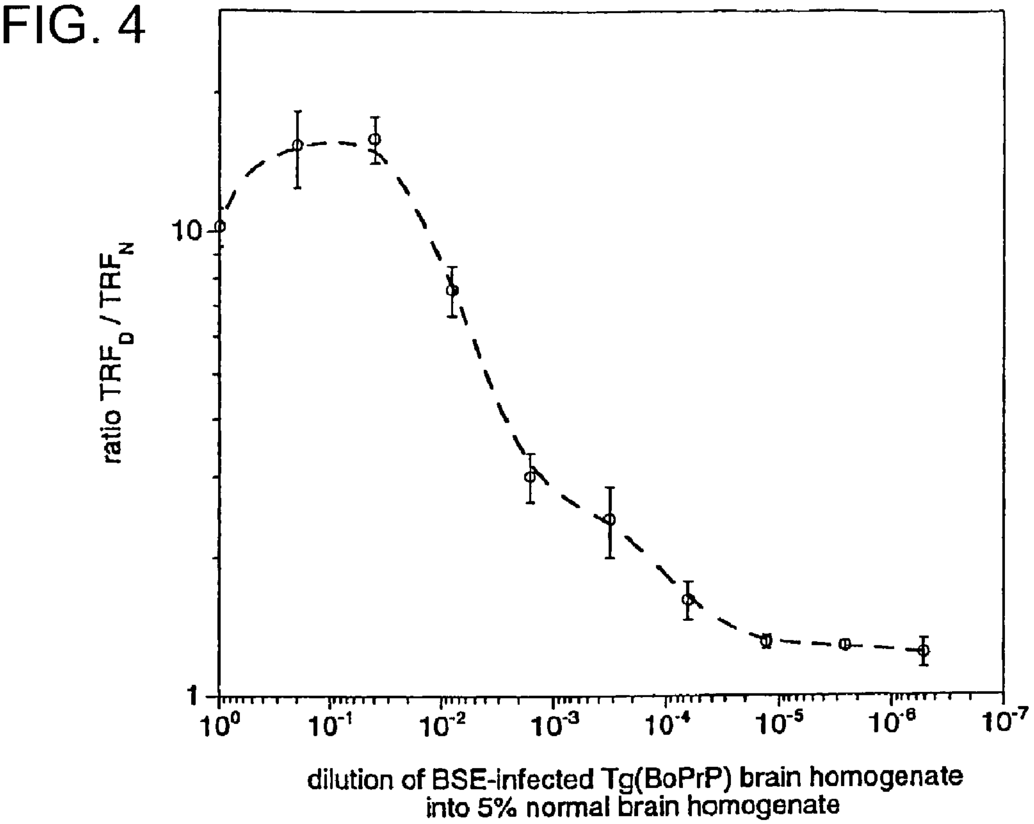
FIGS. 4 and 5 illustrate the sensitivity of CDI for detection of Bovine $PrP^{Sc}$ in the brain homogenates of BSE-infected Tg(BoPrP) mice using Eu-(HuM)Fab P.
Figure 5:
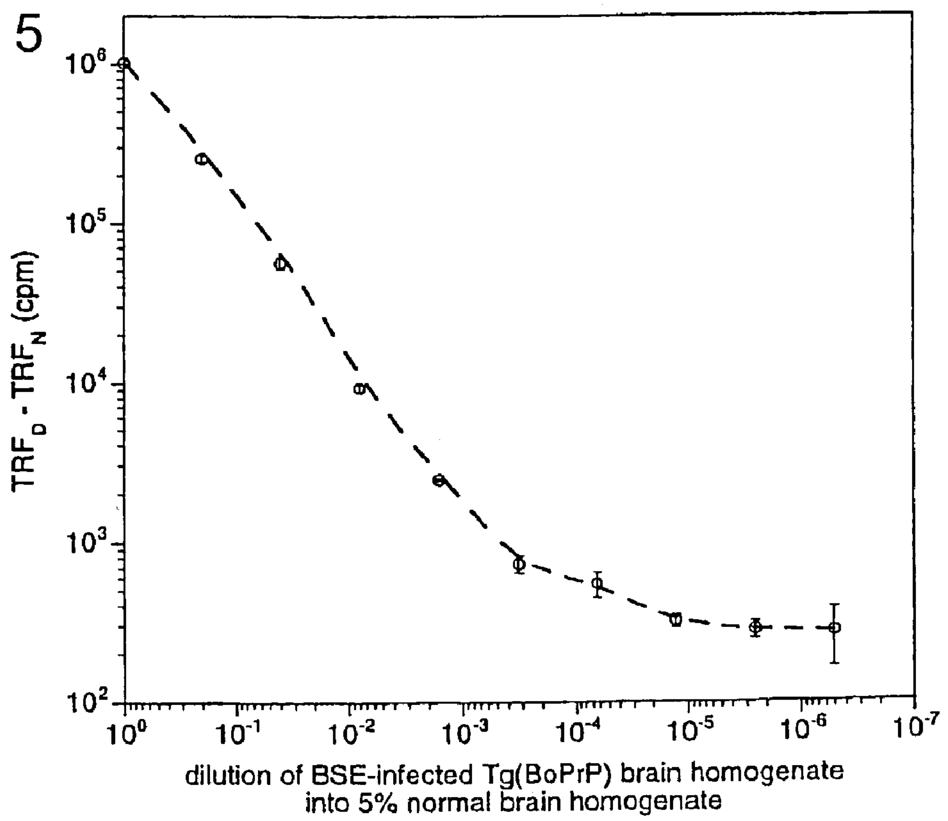

Bovine $PrP^{Sc}$ was detected in BSE-infected Tg(BoPrP) mouse brain homogenates using Eu-(HuM)Fab P. Samples containing serial dilutions of BSE-infected 5% (w/v) brain homogenate in 2% Sarcosyl (w/v), prepared as described in Example 2, were treated with 5 μg/ml of Proteinase K and concentrated with 0.3% (w/v) NaPTA and 1.7 mM $MgCL_2$ prior to CDI. Following PTA precipitation, each sample was divided into two aliquots: (1) untreated and designated native; (2) mixed with final 4M Gdn HCt and heated for 5 min at 80–100° C. and designated denatured. Both samples were diluted 20-fold by $H_2O$ and aliquots loaded on polystyrene plate activated for 1 hr with 0.2% glutaraldehyde in PBS. The plates, incubated overnight at 5° C., were blocked with TBS (pH 7.8), containing 0.5% BSA (w/v) and 6% Sorbitol (w/v). They were then washed three times with TBS (pH 7.8) containing 0.05% (v/v) of Tween 20 and incubated for 2 hrs with Europium-labeled chimeric recombinant Fab P and S. The plates were developed after an additional 7 washing steps in enhancement solution provided by the Europium label supplier (Wallac Inc., Turku, Finland). The signal was evaluated with Discovery (Packard Inc.) time-resolved fluorescence spectroscopy and the PrP concentration was calculated as described (Safar, J., H. Willie, et al. (1998) *Nat. Med*, 4(10):1157–1165). The native and denatured aliquots from each sample were crosslinked to glutaraldehyde-activated ELISA plates and both aliquots were incubated with Europium labeled (HuM)Fab P antibody. After washing, the signal was evaluated with Discovery (Packard Inc.) time-resolved flourescence spectroscopy. The results are expressed as a ratio (FIG. 4) or difference (FIG. 5) of the signals from denatured ($TRF_D$) and native ($TRF_N$) aliquots of each sample. The dynamic range of the detection of $BoPrP^{sc}$ was found to be ≧100,000-fold.

Example 4

Sensitivity of Detection of Bovine $PrP^{sc}$ in Cow Brain Homogenates

Bovine $PrP^{Sc}$ was also detected in homogenates of BSE-infected cows using Eu-(HuM)Fab P. Brains of BSE-infected and normal cows were homogenized on ice by 3×30 second strokes of PowerGen homogenizer (Fisher Scientific, Pittsburgh, Pa.) in PBS (pH 7.4). Resulting 10% (w/v) homogenates were spun for 5 min at 500 g at table top centrifuge. The supernatant was mixed 1:1 with 4% Sarcosyl in PBS (pH 7.4). The 6 BSE-infected brain homogenatse were serially diluted into normal cow brain homogenate and each aliquot was first treated with 5 μg/ml of Proteinase K for 1 hrs at 37° C. After blocking the reaction with 0.5 mM PMSF and Aprotinin and Leupeptin (2 μg/ml each), the samples were precipitated with NaPTA and $MgCl_2$ as described (Safar, J., H. Willie, et al. (1998) *Nat. Med*, 4(10):1157–1165) and each sample was divided into two aliquots: (1) untreated and designated native; (2) mixed with final 4M Gdn HCI and heated for 5 min at 80–100° C. and designated denatured. Both samples were diluted 20-fold by $H_2O$ and aliquots loaded on polystyrene plate activated for 1 hr with 0.2% glutaraldehyde in PBS. The plates, incubated overnight at 5° C., were blocked with TBS (pH 7.8) containing 0.5% BSA (w/V) and 6% Sorbitol (w/v).

Figure 6:
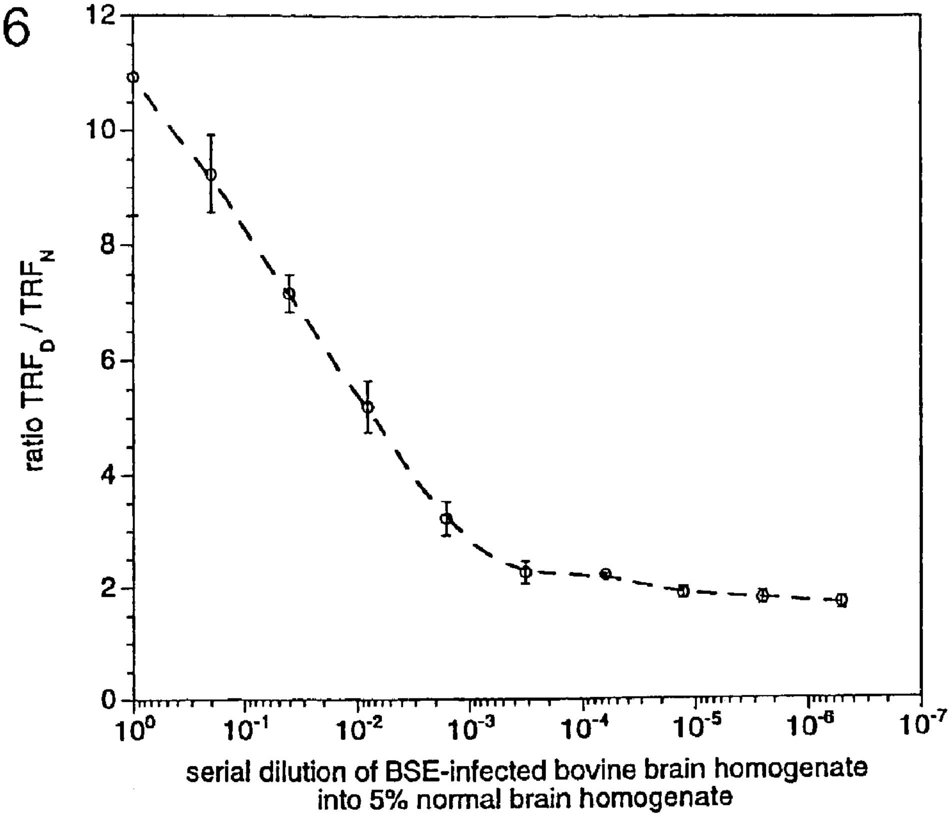
FIGS. 6 and 7 illustrate the sensitivity of CDI for detection of bovine $PrP^{Sc}$ in the brain homogenates of BSE-infected British cows using Eu-(HuM) Fab P.
Figure 7:
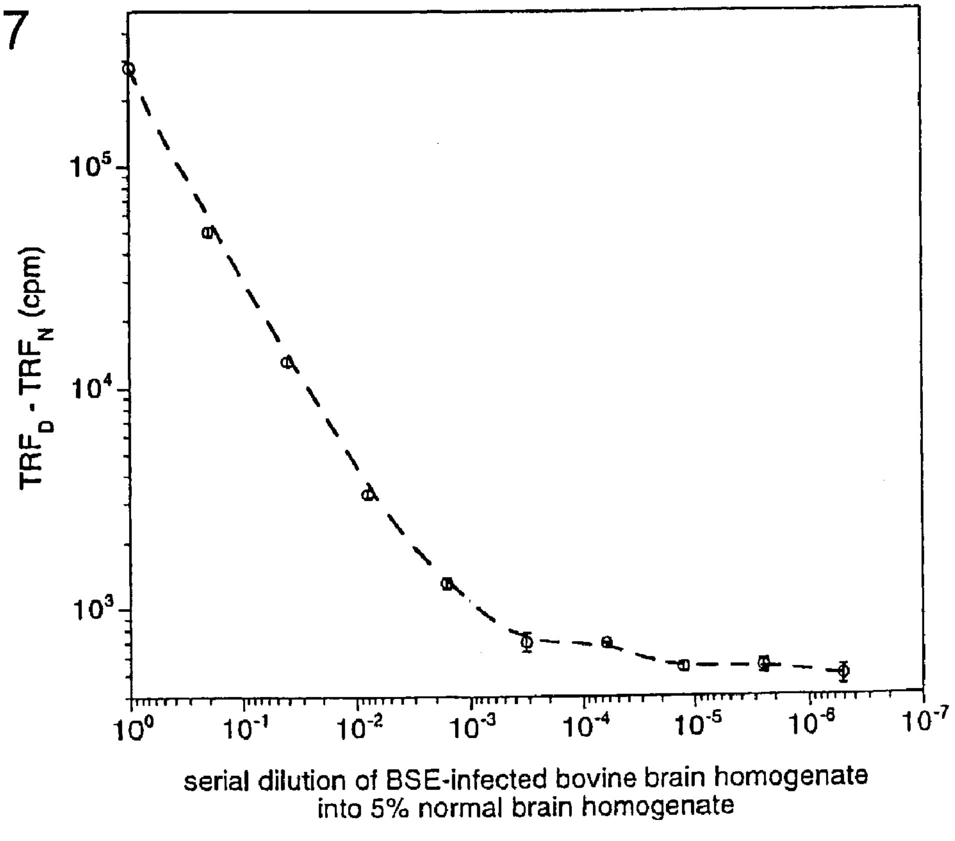

The samples were washed three times with TBS (pH 7.8) containing 0.05% (v/v) of Tween 20 and incubated for 2 hrs with Europium-labeled recombinant chimeric Fab P. The plates were developed after additional washing steps in enhancement solution provided by the Europium label supplier (Wallac Inc., Turku, Finland). The signal was evaluated with Discovery (Packard Inc.) time-resolved fluorescence spectroscopy and the PrP concentration was calculated as described (Safar, J., H. Willie, et al. (1998) *Nat. Med*, 4(10):1157–1165). Bovine $PrP^{Sc}$ was detected in the brain homogenates of BSE-infected British cows using Eu-(HuM) Fab P. Dynamic range of the detection of $BoPRP^{Sc}$ is ≧10,000-fold in samples containing serial dilutions of BSE-infected 5% (w/v) brain homogenate in 2% Sacrosyl (w/v) were treated with 5 μg/ml of Proteinase K and concentrated with 0.3% (w/v) NaPTA and 1.7 mM $MgCL_2$ prior to CDI. The native and denatured aliquots from each sample were incubated with evaluated with Discovery (Packard Inc.) time resolved fluorescence spectroscopy from denatured ($TRF_D$) and native ($TRF_N$) aliquots of each sample. The results are expressed as a ratio (FIG. 6) or difference (FIG. 7) of the signals from denatured ($TRF_D$) and native ($TRF_N$) aliquots of each sample.

Example 5

Strain Sensitivity of Antibody Against Bovine PrPSc in Infected Cow Brain Homogenates Difference in Eu-(HuM)Fab P detection due to differences in BSE strain characteristics was determined using homogenates from 32 different British cows infected with BSE. Brains of 32 BSE-infected cows and 7 normal U.S. control cows were homogenized on ice by 3×30 sec strokes of PowerGen homogenizer (Fisher Scientific, Pittsburgh, Pa.) in PBS (pH 7.4). Resulting 10% (w/v) homogenates was spun for 5 min at 500 g at table top centrifuge. The supernatant was mixed 1:1 with 4% Sarcosyl in PBS (pH 7.4). The BSE-infected brain homogenate was serially diluted into uninoculated Tg(Bo) mice homogenate and each aliquot was first treated with 5 μg/ml of Proteinase K for 1 hrs at 37° C. After blocking the reaction with 0.5 mM PMSF and Aprotinin and Leupeptin (2 μg/ml each), the samples were precipitated with NaPTA and $MgCl_2$ as described (Safar, J., H. Willie, et al. (1998) *Nat. Med*, 4(10):1157–1165) and each sample was divided into two aliquots: (1) untreated and designated native; (2) mixed with final 4M Gdn HCI and heated for 5 min at 80–100° C. and designated denatured. Both samples were diluted 20-fold by $H_2O$ and aliquots loaded an polystyrene plate activated for 1 hr with 0.2% glutaraldehyde in PBS. The plates, incubated overnight at 5° C., were blocked with TBS (pH 7.8) containing 0.5% BSA (w/v) and 6% Sorbitol (w/v).

Figure 8:
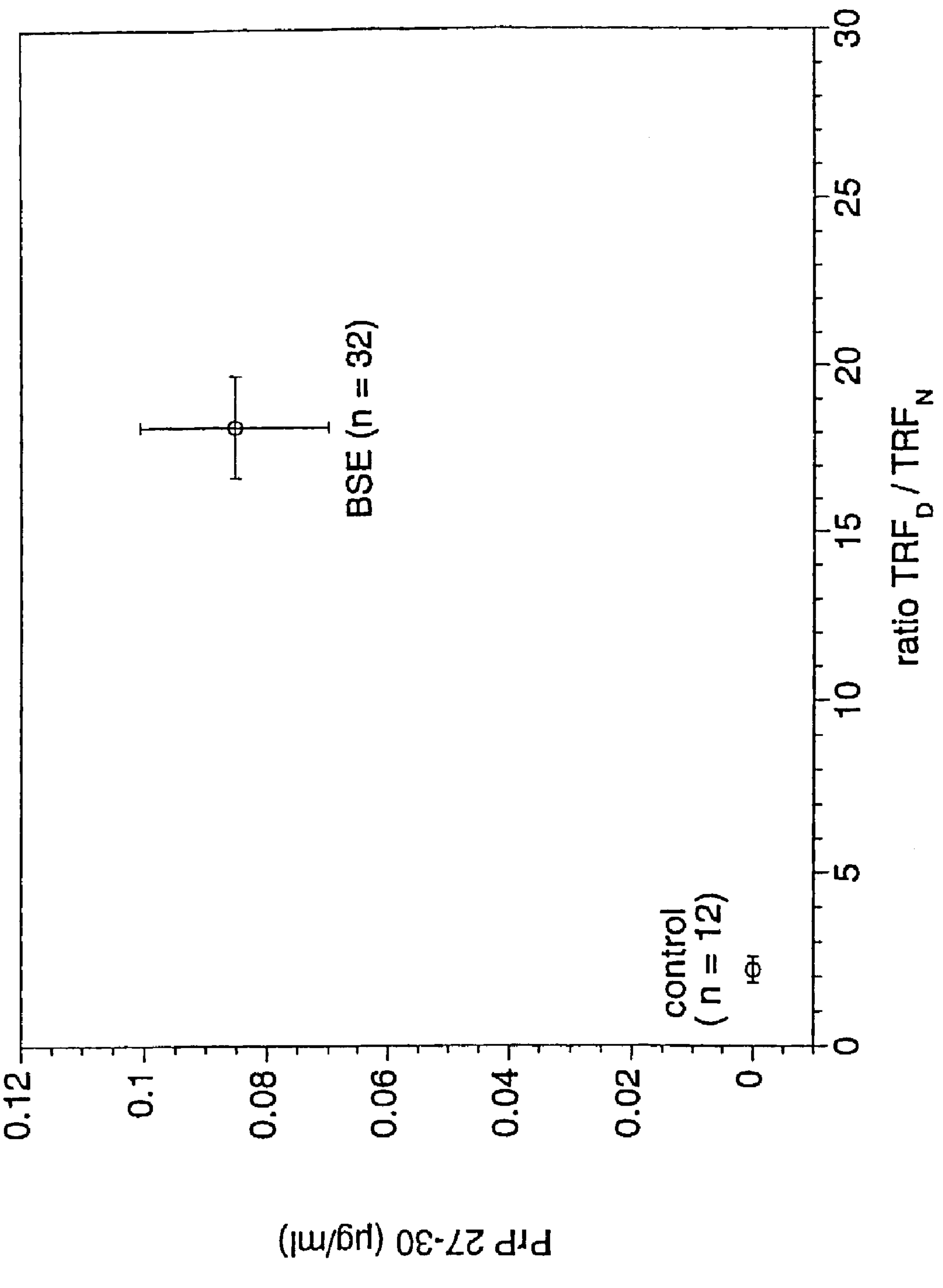
FIG. 8 illustrates the concentration of PrP 27–30 plotted against denatured/native ratio determined by CDI in 32 British cows infected by BSE and 12 noninfected U.S. controls.

The samples were then washed three times with TBS (pH 7.8) containing 0.05% (v/v) of Tween 20 and incubated for 2 hrs with Europium-labeled recombinant chimeric Fab P. The plates were developed after additional washing steps in enhancement solution provided by the Europium label supplier (Wallac Inc., Turku, Finland). The signal was evaluated with Discovery (Packard Inc.) time-resolved fluorescence spectroscopy and the PrP concentration was calculated as described (Safar, J., H. Willie, et al. (1998) *Nat. Med*, 4(10):1157–1165). Concentration of PrP 27–30 plotted against denatured/native ratio determined by CDI in 32 British cows infected by BSE and 12 U.S. controls (FIG. 8). The data are expressed as average±SEM. The concentration of PrP 27–30 was calculated as described previously (Safar, J., H. Willie, et al. (1998) *Nat. Med*, 4(10):1157–1165).

Example 6

Cross-Species Sensitivity of Eu-(HuM)Fab P

Figure 9:
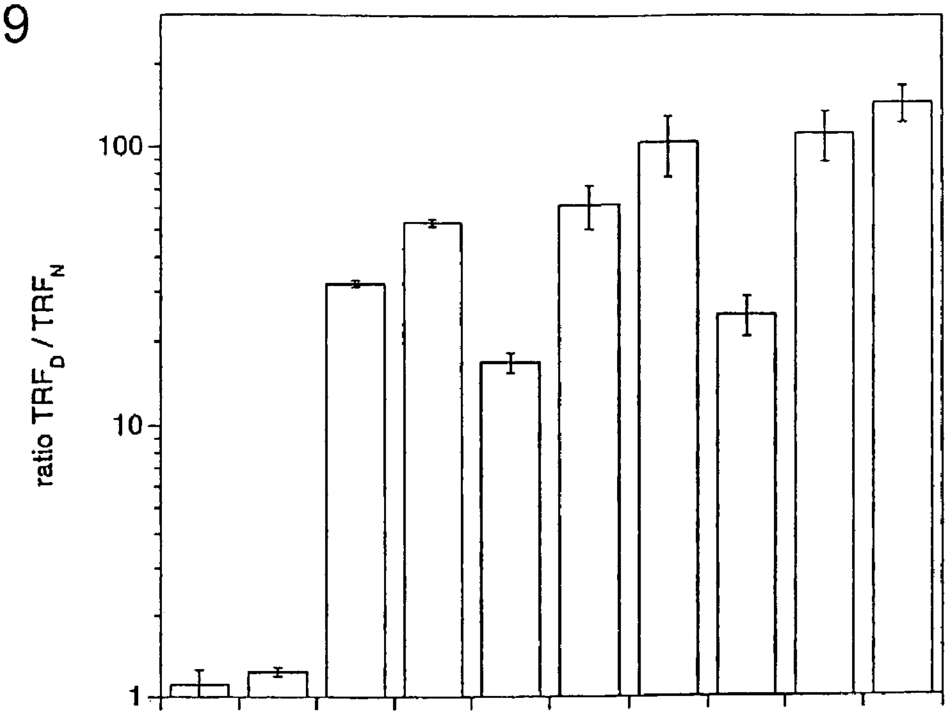
FIGS. 9 and 10 show the results of CDI testing for $PrP^{Sc}$ in chronic wasting diseases (CWD)-infected mule deer, elk, white-tail deer, and normal controls.
Figure 10:
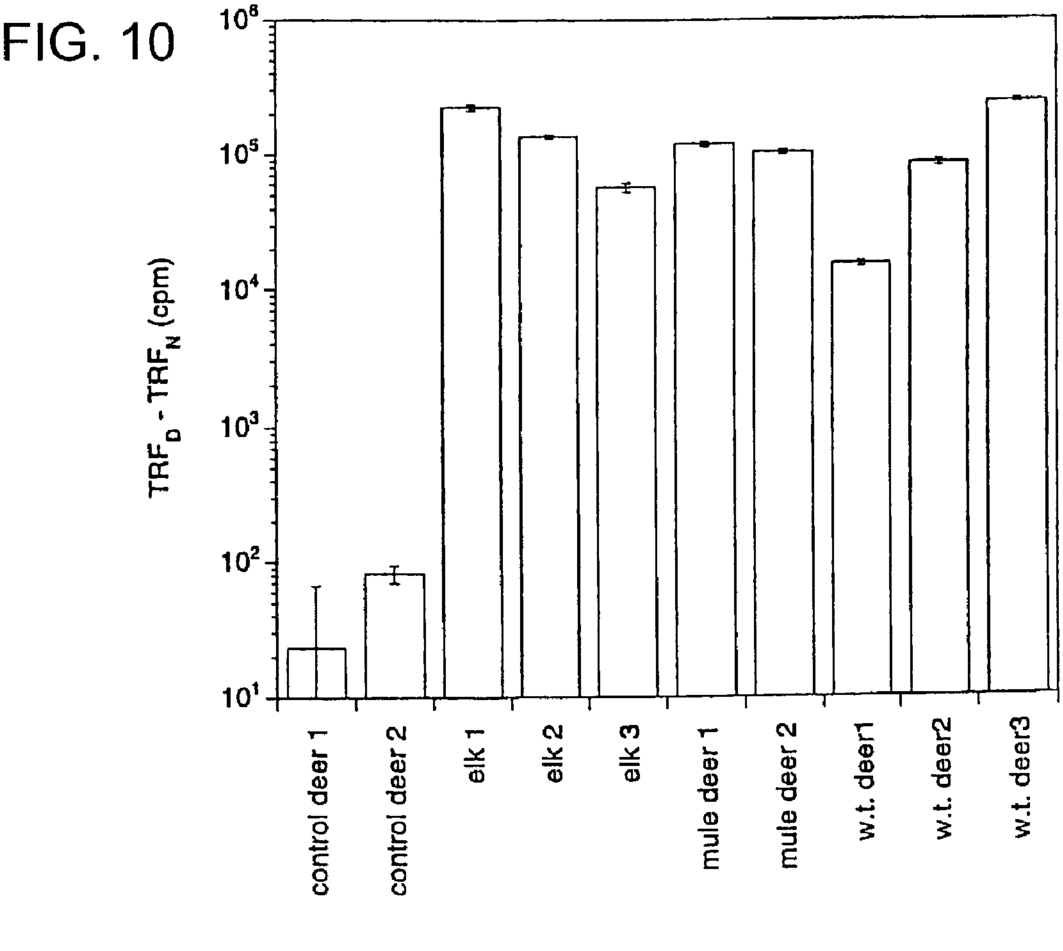

The Eu-(HuM)Fab P antibody was then tested for its ability to detect prion in a variety on ungulate species, including mule deer, elk, and white-tail deer. The brain homogenates of chronic wasting diseases (CWD)-infected mule deer, elk, white-tail deer, and normal controls were treated as in Example 4 to determine the ability of Eu-(HuM) Fab P antibody to recognize prions in these different species. The results of CDI testing for $PrP^{Sc}$ is shown in FIGS. 9 and 10. The results are expressed as a ratio (FIG. 9) or difference (FIG. 10) of the time-resolved fluorescence (TRF) signals from denatured ($TRF_D$) and native ($TRF_N$) aliquots of each sample.

Example 7

Detection of Prions in Deer Infected with CWD

Figure 11:
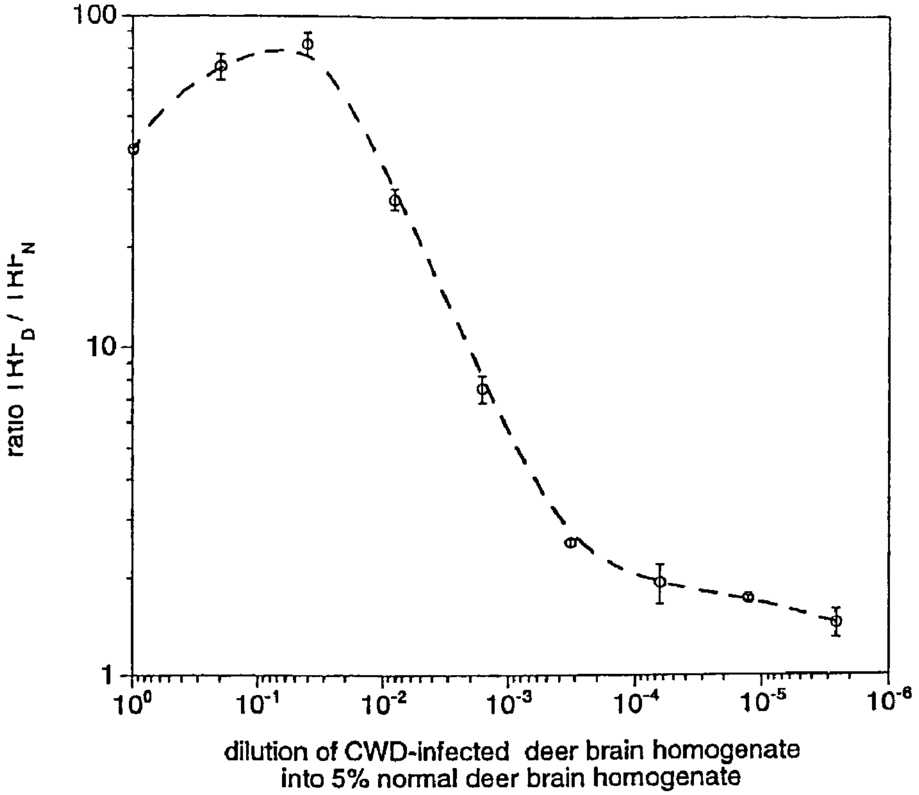
FIGS. 11 and 12 illustrate the sensitivity of CDI for detection of deer $PrP^{Sc}$ in the frontal cortex of CWD-infected deer using Eu-(HuM) Fab P. Dynamic range of the detection of deer $PrP^{Sc}$ is $\geqq$100,000-fold.
Figure 12:
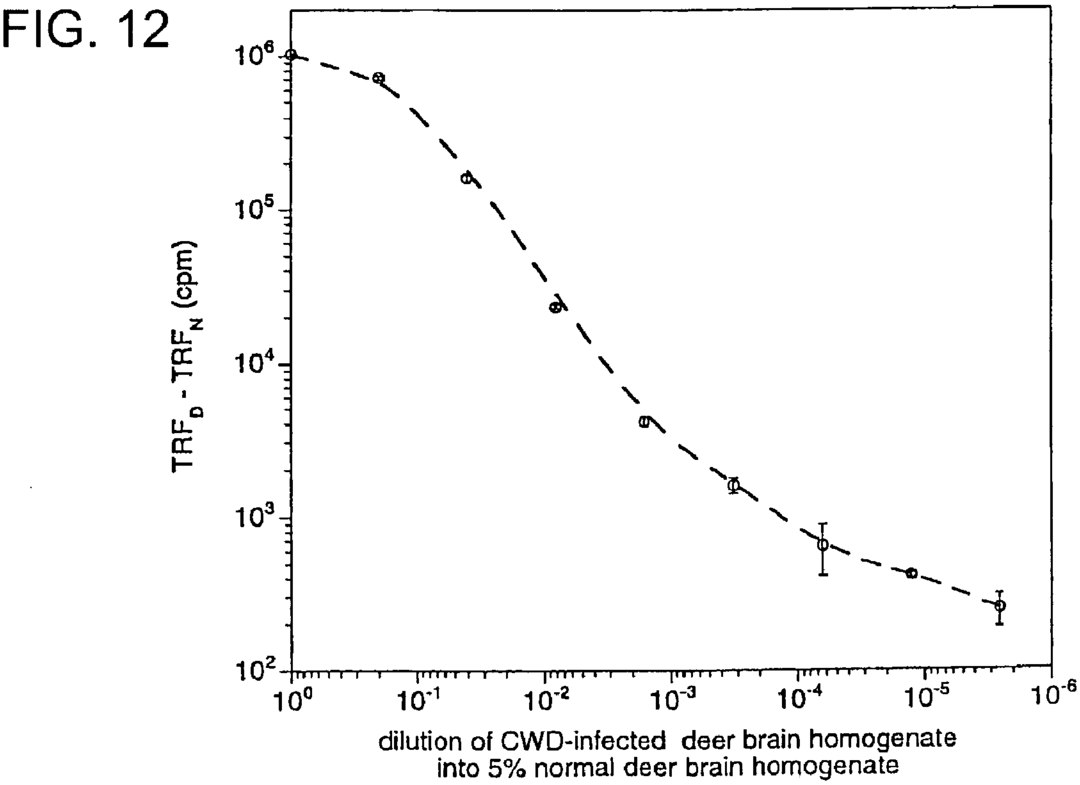

Deer $PrP^{Sc}$ was detected in homogenates of CWD-infected deer using Eu-(HuM)Fab P. Samples containing serial dilutions of CWD-infected 5% (w/v) brain homogenate in 2% Sacrosyl (w/v) were treated with 5 μg/ml of Proteinase K and concentrated with 0.3% (w/v) NaPTA and 1.7 mM $MgCL_2$ prior to CDI. The native and denatured aliquots from each sample were crosslinked to glutaraldehyde-activated ELISA plate and both aliquots were incubated with Europium labeled (HuM)Fab P antibody. After 7 washing steps, the signal was evaluated with Discovery (Packard Inc.) time-resolved fluorescence spectroscopy. The results are expressed as a ratio (FIG. 11) or difference (FIG. 12) of the signals from denatured ($TRF_D$) and native $TRF^N$) aliquots of each sample.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of detecting ungulate $PrP^{Sc}$, comprising the steps of:

providing a sample suspected of containing ungulate $PrP^{Sc}$ and ungulate $PrP^{C}$;

dividing the sample into a first portion and a second portion;

contacting the first portion with a labeled antibody which binds to native ungulate $PrP^{C}$ with a binding affinity of $K_a$ of $10^8$ l/mol or more wherein the antibody is further characterized by not binding to $PrP^{C}$ of a mammal other than a ungulate;

treating the second portion in a manner in which causes any ungulate $PrP^{Sc}$ to assume a confirmation which binds to the antibody which binds to native ungulate $PrP^{C}$;

contacting the treated second portion with the labeled antibody;

determining the level of binding of labeled antibody to $PrP^{C}$ in the first portion;

determining the level of binding of labeled antibody to treated PrP protein in the second portion; and comparing the level of binding of labeled antibody to PrP protein in the first portion with the level of binding to labeled antibody in the second portion and thereby determining whether the sample comprises ungulate $PrP^{Sc}$ protein.

2. The method as claimed in claim 1, wherein the antibody binds to native ungulate $PrP^{Sc}$ with a binding affinity Of $K_a$ of $10^6$ l/mol or less.

3. The method as claimed in claim 1, further comprising:

homogenizing the sample prior to dividing the sample into a first portion and a second portion.

4. The method as claimed in claim 3, wherein the homogenized sample is treated with a binding agent which binds ungulate $PrP^{Sc}$ in the sample.

5. The method as claimed in claim 4, wherein the binding agent is phosphotungstic acid (PTA).

6. A method of detecting ungulate $PrP^{Sc}$, comprising the steps of:

providing a sample suspected of containing ungulate $PrP^{Sc}$ and ungulate $PrP^{C}$;

dividing the sample into a first portion and a second portion;

contacting the first portion with a labeled antibody which binds to native ungulate $PrP^{C}$ with a binding affinity of $K_a$ of $10^8$ l/mol or more wherein the antibody is further characterized by not binding to $PrP^{C}$ of a mammal other than a ungulate;

treating the second portion in a manner in which causes any ungulate $PrP^{Sc}$ to assume a confirmation which binds to the antibody which binds to native ungulate $PrP^{C}$;

contacting the treated second portion with the labeled antibody;

determining the level of binding of labeled antibody to $PrP^{C}$ in the first portion;

determining the level of binding of labeled antibody to treated PrP protein in the second portion;

adjusting the determined level of binding of labeled antibody to treated PrP protein in the second portion to compensate for increasing binding affinity of $PrP^{C}$ protein resulting from the treating; and comparing the level of binding of labeled antibody to PrP protein in the first portion with the level of binding to labeled antibody in the second portion and thereby determining whether the sample comprises ungulate $PrP^{Sc}$ protein.

7. The method as claimed in claim 6, wherein the antibody binds to native ungulate $PrP^{Sc}$ with a binding affinity Of $K_a$ of $10^6$ l/mol or less.

8. The method as claimed in claim 6, further comprising:

homogenizing the sample prior to dividing the sample into a first portion and a second portion.

9. The method as claimed in claim 8, wherein the homogenized sample is treated with a binding agent which binds ungulate $PrP^{Sc}$ in the sample.

10. The method as claimed in claim 9, wherein the binding agent is phosphotungstic acid (PTA).

11. The method of claim 1, wherein levels of binding of labeled antibody to PrP protein are determined using flow cytometry.

12. The method of claim 6, wherein levels of binding of labeled antibody to PrP protein are determined using flow cytometry, and the labeled antibody is fluorescence labeled.

13. The method of claim 1, wherein the labeled antibody is Europium-labeled.

14. The method of claim 12, wherein the labeled antibody is Europium-labeled.

15. The method of claim 1, wherein levels of binding of labeled antibody to PrP protein are determined using time-resolved, dissociation-enhanced fluorescence.

16. The method of claim 6, wherein levels of binding of labeled antibody to PrP protein are determined using time-resolved, dissociation-enhanced fluorescence.

17. The method of claim 10, wherein levels of binding of labeled antibody to PrP protein are determined using time-resolved, dissociation-enhanced fluorescence.

18. The method of claim 10, further comprising:

adjusting the determined level of binding of labeled antibody to treated PrP protein in the second portion to compensate for increasing the affinity of the $PrP^{C}$ protein for the antibody resulting from the treating.

19. The method of claim 6, wherein the ungulate is selected from the group consisting of a cow, a sheep, a deer, an elk and a horse.

20. An assay, comprising:

a support surface; and an antibody bound to the surface of the support, the antibody characterized by an ability to bind denatured ungulate $PrP^{Sc}$ with a binding affinity of $10^7$ l/mole or more wherein the antibody is further characterized by not binding to $PrP^{C}$ of a mammal other than a ungulate.

21. The assay of claim 20, wherein the antibody is characterized by an ability to bind 50% or more denatured ungulate $PrP^{Sc}$ in a liquid flowable sample.

22. The assay of claim 20, wherein a plurality of different antibodies are bound to the support surface and each antibody has a $K_a$ of $10^7$ l/mole or more relative to $PrP^{Sc}$.

23. A method of detecting prions in an ungulate, comprising:

extracting tissue from an animal;

dividing the sample into a first portion and a second portion;

contacting a the first portion with an antibody characterized by its ability to bind a native cow $PrP^{C}$ in situ wherein the antibody is further characterized by not binding to $PrP^{C}$ of a mammal other than a ungulate to determine the a first PrP level;

treating a second portion to denature $PrP^{Sc}$ present in the second portion; and contacting the denatured second sample of the tissue with the antibody to determine a second PrP level;

wherein the presence of $PrP^{Sc}$ in said sample is detected by subtracting the first level from the second level and considering an effect on the treating on the second PrP level.

24. The method of claim 23, wherein the tissue is brain tissue and is extracted from a dead ungulate.

* * * * *

SEQUENCE LISTING

<160> NUMBER OF SEQ ID NOS: 11

<210> SEQ ID NO 1
<211> LENGTH: 112
<212> TYPE: PRT
<213> ORGANISM: Artificial Sequence
<220> FEATURE:
<223> OTHER INFORMATION: synthesized peptide

<400> SEQUENCE: 1

```
Glu Leu Val Met Thr Gln Thr Pro Ser Ser Leu Ser Ala Ser Leu Gly
 1               5                  10                  15

Glu Arg Val Ser Leu Thr Cys Arg Ala Ser Gln Asp Ile Gly Asn Asn
            20                  25                  30

Leu Asn Trp Ile Gln Gln Lys Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln His Asp Thr Phe Pro Leu
                85                  90                  95

Thr Phe Gly Gly Gly Thr Lys Leu Glu Ile Lys Arg Thr Val Ala Ala
            100                 105                 110
```

<210> SEQ ID NO 2
<211> LENGTH: 44
<212> TYPE: PRT
<213> ORGANISM: Artificial Sequence
<220> FEATURE:
<223> OTHER INFORMATION: synthesized peptide

<400> SEQUENCE: 2

```
Glu Val Gln Leu Leu Glu Gln Ser Gly Ala Glu Leu Val Lys Pro Gly
 1               5                  10                  15

Ala Ser Val Lys Leu Ser Cys Thr Ala Ser Gly Phe Asn Ile Glu Asp
            20                  25                  30

Ser Tyr Ile His Trp Val Lys Gln Arg Pro Glu Gln
        35                  40
```

<210> SEQ ID NO 3
<211> LENGTH: 44
<212> TYPE: PRT
<213> ORGANISM: Artificial Sequence
<220> FEATURE:
<223> OTHER INFORMATION: synthesized peptide

<400> SEQUENCE: 3

```
Glu Val Gln Leu Leu Glu Gln Ser Gly Ala Glu Leu Val Arg Pro Gly
 1               5                  10                  15

Ala Ser Val Lys Leu Ser Cys Thr Ala Ser Gly Phe Asn Ile Glu Asp
            20                  25                  30

Tyr Tyr Ile His Trp Val Ile Gln Arg Pro Gly Gln
        35                  40
```

<210> SEQ ID NO 4
<211> LENGTH: 45
<212> TYPE: PRT
<213> ORGANISM: Artificial Sequence
<220> FEATURE:

-continued

<223> OTHER INFORMATION: synthesized peptide

<400> SEQUENCE: 4

```
Gly Leu Glu Trp Ile Gly Arg Ile Asp Pro Glu Asp Gly Glu Thr Lys
 1               5                  10                  15

Tyr Ala Pro Lys Phe Gln Gly Lys Ala Thr Ile Thr Ala Asp Thr Ser
            20                  25                  30

Ser Asn Thr Ala Tyr Leu His Leu Arg Arg Leu Thr Ser
        35                  40                  45
```

<210> SEQ ID NO 5
<211> LENGTH: 45
<212> TYPE: PRT
<213> ORGANISM: Artificial Sequence
<220> FEATURE:
<223> OTHER INFORMATION: synthesized peptide

<400> SEQUENCE: 5

```
Gly Leu Glu Trp Ile Gly Arg Ile Asp Pro Glu Asp Gly Glu Thr Lys
 1               5                  10                  15

Tyr Ala Pro Lys Phe Gln Asp Lys Ala Thr Leu Thr Ala Asp Thr Ser
            20                  25                  30

Ser Asn Thr Ala Tyr Leu His Leu Arg Ser Leu Thr Ser
        35                  40                  45
```

<210> SEQ ID NO 6
<211> LENGTH: 34
<212> TYPE: PRT
<213> ORGANISM: Artificial Sequence
<220> FEATURE:
<223> OTHER INFORMATION: synthesized peptide

<400> SEQUENCE: 6

```
Glu Asp Thr Ala Ile Tyr Tyr Cys Gly Arg Gly Ala Tyr Tyr Ile Lys
 1               5                  10                  15

Glu Asp Phe Trp Gly Gln Gly Thr Thr Leu Thr Val Ser Ser Ala Ser
            20                  25                  30

Thr Lys
```

<210> SEQ ID NO 7
<211> LENGTH: 35
<212> TYPE: PRT
<213> ORGANISM: Artificial Sequence
<220> FEATURE:
<223> OTHER INFORMATION: synthesized peptide

<400> SEQUENCE: 7

```
Glu Asp Thr Ala Ile Tyr Phe Cys Gly Arg Asn Asp Gly Leu Tyr Ala
 1               5                  10                  15

Gly Gln Asp Tyr Trp Gly Gln Gly Thr Thr Leu Thr Val Ser Ser Ala
            20                  25                  30

Ser Thr Lys
        35
```

<210> SEQ ID NO 8
<211> LENGTH: 14
<212> TYPE: PRT
<213> ORGANISM: Artificial Sequence
<220> FEATURE:
<223> OTHER INFORMATION: consensus epitope

<400> SEQUENCE: 8

-continued

```
His Gly Ser Gln Trp Asn Lys Pro Ser Lys Pro Lys Thr Asn
 1               5                  10


<210> SEQ ID NO 9
<211> LENGTH: 14
<212> TYPE: PRT
<213> ORGANISM: Artificial Sequence
<220> FEATURE:
<223> OTHER INFORMATION: Consensus epitope

<400> SEQUENCE: 9

His Gly Asn Gln Trp Asn Lys Pro Ser Lys Pro Lys Thr Asn
 1               5                  10


<210> SEQ ID NO 10
<211> LENGTH: 254
<212> TYPE: PRT
<213> ORGANISM: Mus musculus

<400> SEQUENCE: 10

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250


<210> SEQ ID NO 11
<211> LENGTH: 264
<212> TYPE: PRT
<213> ORGANISM: Bos taurus

<400> SEQUENCE: 11
```

-continued

```
Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
            20                  25                  30

Trp Asn Thr Gly Gly Ser Arg Tyr Pro Gly Gln Gly Ser Pro Gly Gly
        35                  40                  45

Asn Arg Tyr Pro Pro Gln Gly Gly Gly Gly Trp Gly Gln Pro His Gly
    50                  55                  60

Gly Gly Trp Gly Gln Pro His Gly Gly Gly Trp Gly Gln Pro His Gly
65                  70                  75                  80

Gly Gly Trp Gly Gln Pro His Gly Gly Gly Trp Gly Gln Pro His Gly
                85                  90                  95

Gly Gly Gly Trp Gly Gln Gly Gly Thr His Gly Gln Trp Asn Lys Pro
            100                 105                 110

Ser Lys Pro Lys Thr Asn Met Lys His Val Ala Gly Ala Ala Ala Ala
        115                 120                 125

Gly Ala Val Val Gly Gly Leu Gly Gly Tyr Met Leu Gly Ser Ala Met
    130                 135                 140

Ser Arg Pro Leu Ile His Phe Gly Ser Asp Tyr Glu Asp Arg Tyr Tyr
145                 150                 155                 160

Arg Glu Asn Met His Arg Tyr Pro Asn Gln Val Tyr Tyr Arg Pro Val
                165                 170                 175

Asp Gln Tyr Ser Asn Gln Asn Asn Phe Val His Asp Cys Val Asn Ile
            180                 185                 190

Thr Val Lys Glu His Thr Val Thr Thr Thr Thr Lys Gly Glu Asn Phe
        195                 200                 205

Thr Glu Thr Asp Ile Lys Met Met Glu Arg Val Val Glu Gln Met Cys
    210                 215                 220

Ile Thr Gln Tyr Gln Lys Glu Ser Gln Ala Tyr Tyr Asp Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260
```